United States Patent
Hett et al.

(10) Patent No.: US 12,116,344 B2
(45) Date of Patent: Oct. 15, 2024

(54) CRYSTALLINE FORMS OF A PHARMACEUTICAL COMPOUND

(71) Applicant: Azafaros B.V., Leiden (NL)

(72) Inventors: Robert Hett, Leiden (NL); Fritz Blatter, Leiden (NL); Jennifer Robin, Leiden (NL); Kyle Landskroner, Basel (CH)

(73) Assignee: Azafaros B.V., Leiden (NL)

( * ) Notice: Subject to any disclaimer, the term of this patent is extended or adjusted under 35 U.S.C. 154(b) by 0 days.

(21) Appl. No.: 18/029,842

(22) PCT Filed: Oct. 1, 2021

(86) PCT No.: PCT/EP2021/077100
§ 371 (c)(1),
(2) Date: Mar. 31, 2023

(87) PCT Pub. No.: WO2022/069709
PCT Pub. Date: Apr. 7, 2022

(65) Prior Publication Data
US 2023/0391724 A1   Dec. 7, 2023
US 2024/0287001 A9   Aug. 29, 2024

(30) Foreign Application Priority Data
Oct. 2, 2020 (EP) .................... 20199934

(51) Int. Cl.
C07D 211/46   (2006.01)
(52) U.S. Cl.
CPC ........ *C07D 211/46* (2013.01); *C07B 2200/13* (2013.01)
(58) Field of Classification Search
None
See application file for complete search history.

(56) References Cited

FOREIGN PATENT DOCUMENTS

| WO | WO 2015/147639 | * 10/2015 | ........... C07D 211/46 |
| WO | 2016209080 | 12/2016 | |

OTHER PUBLICATIONS

Asahara (1985) Teruzo, Solvent Handbook, pp. 47-51.
The Chemical Society of Japan, 4th Edition, Experiment Chemistry Course 1, Basic Operation I, 2nd printing, Maruzen Co., Ltd., Apr. 5, 1996, pp. 184-186.
Lahav et al. (2017) A Fluorescence Polarization Activity-Based Protein Profiling Assay in the Discovery of Potent, Selective Inhibitors for Human Nonlysosomal Glucosylceramidase, J. Am. Chem. Soc., vol. 139, pp. 14192-14197.
Notice of Reasons for Rejection dated Jun. 13, 2023, Appl. No. JP P2022-577645, 5 pp.
Takata (2007) API Form screening and selection in drug discovery stage, Pharm Stage, vol. 6, No. pp. 20-25.
Caira (1998) "Crystalline Polymorphism of Organic Compounds" Topics in Current Chemistry, 198:163-208.
Ghisaidoobe et al. (2014) "Identification and Development of Biphenyl Substituted Iminosugars as Improved Dual Glucosylceramide Synthase/Neutral Glucosylceramidase Inhibitors" Journal of Medicinal Chemistry, 57 (21):9096-9104.
International Preliminary Report on Patentability dated Jul. 18, 2022, Appl. No. PCT/EP2021/077100, 11 pp.
Lahav et al. (2017) "Supporting Information a Fluorescence Polarization Activity-Based Protein Profiling Assay in the Discovery of Potent, Selective Inhibitors for Human Non-lysosomal Glucosylceramidase" Journal of the American Chemical Society, pp. S1-S207.
Anderson (2011) "Practical Process Research and Development: a Guide for Organic Chemists" Science Press, 1st edition, pp. 172-175 (including translation).
First Office Action and Search Report dated Jan. 1, 2024, Appl. No. CN 202180067242.0, 11 pp.
Zhang et al. (2006) "Organic Chemistry Experiments" 1st edition, China Medical Science Press, pp. 35-38 (including translation).
Detoisien et al. (2009) "A Rapid Method for Screening Crystallization Conditions and Phases of an Active Pharmaceutical Ingredient" Organic Process Research & Development, 13:1338-1342.
Office Action (English Translation) dated Jul. 19, 2024, Appl. No. EA 202392529, 3 pp.

* cited by examiner

*Primary Examiner* — Craig D Ricci
(74) *Attorney, Agent, or Firm* — Brian E. Davy; Bozicevic, Field & Francis LLP

(57) ABSTRACT

The present invention relates to a crystalline form of compound (I) and a method of making the crystalline form of compound (I). The invention also provides pharmaceutical compositions comprising the crystalline form of compound (I). Furthermore, the invention relates to methods of using this crystalline form of compound (I) as a medicament and in the treatment of a disease involving abnormal levels of glucosylceramide and/or higher levels of glycosphingolipids.

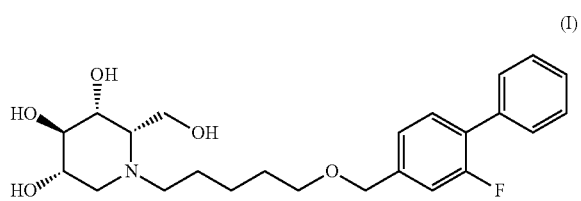

5 Claims, 17 Drawing Sheets

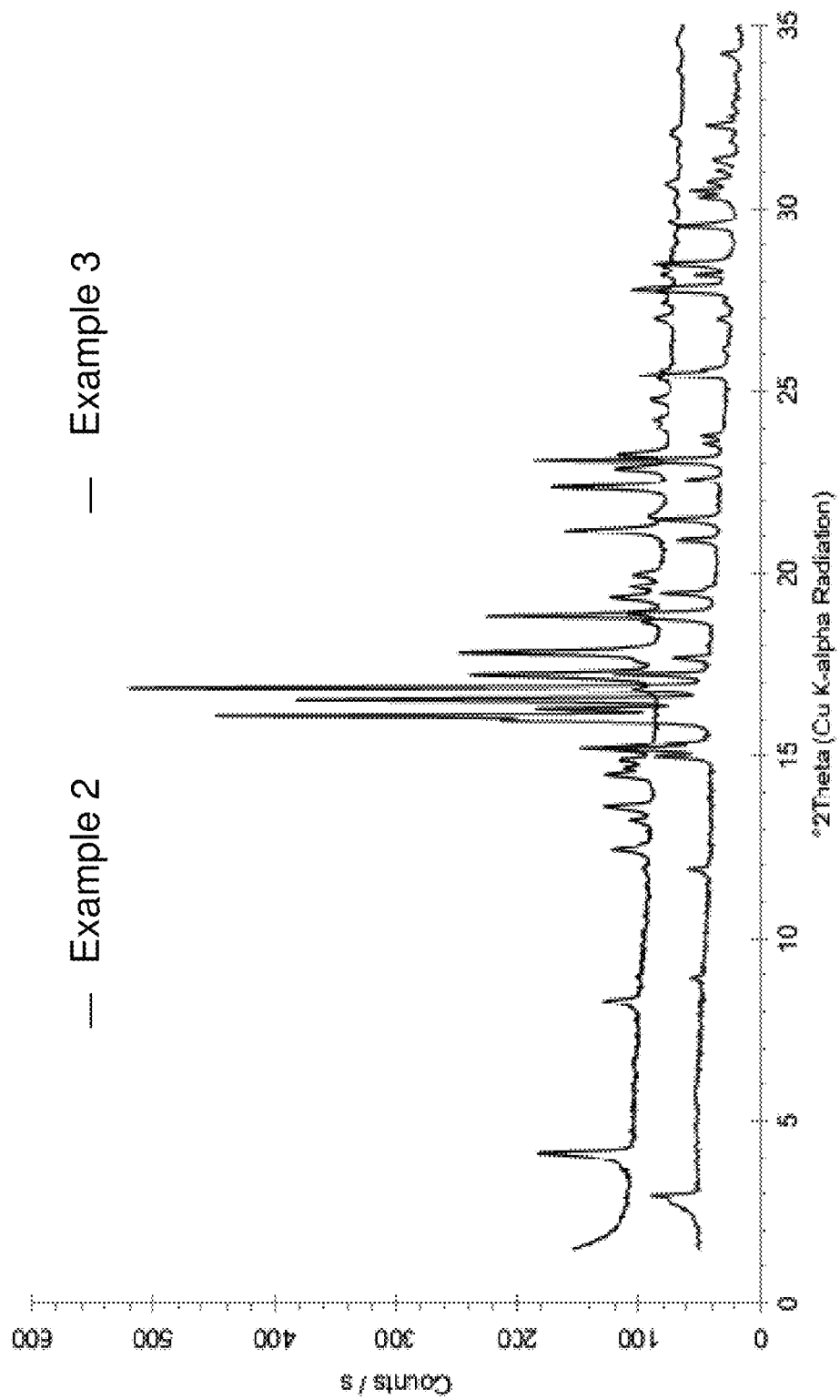

| Evaluation, measures | Sum of scores |
|---|---|
| Stress level 0 = no stress | 0 |
| Stress level 1 = light level of stress, to be observed carefully | 1-9 |
| Stress level 2 = moderate level of stress, the veterinarian must be informed | 10-19 |
| Stress level 3 = high level of stress, the veterinarian and the study director must be informed, veterinary care or rather euthanasia if required | 20 or more |

*Make a note under Remarks (deviations of following criteria for clinical examination or symptoms)

| a: weight loss | c: locomotion | e: fur/skin surface | g: abdomen | i: behavior/activity |
|---|---|---|---|---|
| b: posture | d: eye | f: dehydration | h: respiration | k: temperature |
| m: Tremor | | o: rectal prolapse | p: penile prolaps | s: study specific |

| Project no.: | Line: NPC1 | Date: | Time: | Experimenter (name / paraphe): |

| Cohort | | | | | | | | | | | | | | | | |
|---|---|---|---|---|---|---|---|---|---|---|---|---|---|---|---|---|
| Group | | | | | | | | | | | | | | | | |
| Parameter | IRN | | | | | | | | | | | | | | | |
| | | | Weight loss | | | | General health/ activity | | | Clinical findings | | | | Line specific | | |
| | unaffected or weight gain | alteration < 5% | Weight loss 5-10% | Weight loss 11-20% | Weight loss > 20% | smooth and shiny fur, normal activity | rough hair coat, cloudy eyes | small wounds, dirty hair coat, moderate level of prolapse, abnormal posture, reduced activity | humid neglected orifices, dehydration, hunched posture, high level of prolapse, isolation (severe reduced activity) | normal temperature and respiration | Slight deviations of the normal situation | the animal feels colder as normal, cold extremities, rapid shallow breathing | moderate deviation of the temperature or respiration, enlarged abdomen | severe deviation of the temperature or respiration (severe labored breathing) | Presence of righting reflux, normal movement | slight incoordination, slight-moderate tremor | high level of Tremor, incoordinated movement | Reduced righting reflex | Body weight loss > 1g within 24h, loss of righting reflex |
| Score | 0 | 1 | 5 | 10 | 20 | 0 | 1 | 5 | 10 | 0 | 1 | 5 | 10 | 20 | 0 | 1 | 5 | 10 | 20 |
| | | | | | | | | | | | | | | | SUM of SCORES | | | | |
| | | | | | | | | | | | | | | | Remarks (specify the clinical signs)* | | | | |

CRYSTALLINE FORMS OF A PHARMACEUTICAL COMPOUND

FIELD OF THE INVENTION

The invention relates to a crystalline form of compound (I),

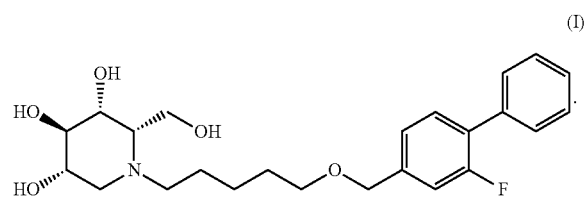 [SMILES: OC[C@H]1[C@@H](O)[C@H](O)[C@@H](O)CN1CCCCCOCc1ccc(-c2ccccc2)c(F)c1]

(I)

The invention also relates to a method of making the crystalline form of compound (I), as well as pharmaceutical compositions comprising the crystalline form of compound (I).

Furthermore, the invention relates to methods of using this crystalline form of compound (I) as a medicament and in the treatment of a disease involving abnormal levels of glucosylceramide and/or higher levels of glycosphingolipids.

BACKGROUND TO THE INVENTION

A crystal state of a compound can be important when the compound is used for pharmaceutical purposes. This is because the morphology, particle size, polymorphism, solvation, or hydration of the crystal state of a compound can affect filtration, flow, tableting, dissolution and bioavailability of a pharmaceutical agent.

Deoxynojirimycin derivatives are an important class of molecules in medicinal chemistry and drug discovery. N-(Hydroxyethyl)-deoxynojirimycin is marketed as Miglitol as an antidiabetic agent for type 2 diabetes. Miglitol also acts as a broad-spectrum inhibitor of several intestinal glycosidases (maltase, sucrose and lactase) (Hillebrand et al., Diabetes, 1986, Vol. 35, A93-A93) (Scott and Spencer, Drugs, 2000, Vol. 59, 521-549).

N-butyl-deoxynojirimycin (miglustat, Zavesca®) was developed as an inhibitor of glucosylceramide synthase (also called ceramide glucosyltransferase, EC 2.4.1.80, UniProt code: Q16739) and is used in clinics to treat patients with the lysosomal storage disorder, Gaucher disease (Platt et al., J. Biol. Chem., 1994, Vol. 269, 8362-8365) (Cox et al., Lancet, 2000, Vol. 355, 1481-1485) and Niemann-Pick type C disease (Pineda et al. Orphanet J. Rare Dis., 2018, Vol. 13, 140).

WO2015/147639 A1 describes novel derivatives of deoxynojirimycin, including compound (I),

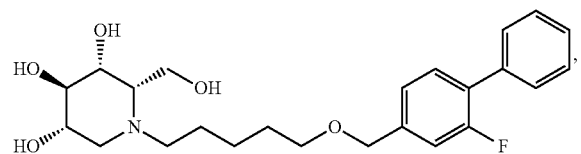

(I)

which are effective in the treatment of diseases that are associated with abnormal levels of cytosolic or lysosomal glucosylceramide and/or higher levels of glycosphingolipids. Compound (I) is a potent dual inhibitor of glucosylceramide synthase and non-lysosomal glucosylceramidase (GBA2, UniProt code: Q9HCG7).

Therapeutic compounds useful in treating the abnormal levels of glucosylceramide and/or higher levels of glycosphingolipids are often administered in the form of tablets. When preparing pharmaceutical compositions and formulations for use in such tablets, it is highly desirable to have a crystalline form of the therapeutic compound having low levels of hygroscopicity and/or low levels of deliquescence thereby allowing the compound to be compressed into a desired shape or size.

Furthermore, a relatively high melting point (typically greater than about 80° C.) of a therapeutic compound favours resistance to decomposition thereby facilitating the storage and increasing shelf life of the therapeutic compound, which is desirable for any pharmaceutical agent.

It is also particularly beneficial that a therapeutic compound is non-hygroscopic, or substantially non-hygroscopic, when considering the handling, manufacturing, and storage of the pharmaceutical agent. If a pharmaceutical agent shows hygroscopic properties, many problems may arise, for example:

difficulty with reduction of material into small particles or powder by crushing;

unwanted moisture hindering appropriate reactions and forming unwanted end products, which results in minimum quality and reduced shelf life;

production of soft tablets during manufacturing, or penetration of moisture inside the packaging;

powders adhering to the conveyor, which can influence the process of filling.

Thus, it is desirable to have a crystalline form of the therapeutic compound that is non-hygroscopic or substantially non-hygroscopic.

No crystalline forms of compound (I) have been reported previously. Accordingly, a need exists for stable and/or non-deliquescent crystalline forms of compound (I), which are preferably substantially non-hygroscopic and/or have relatively high melting points.

SUMMARY OF THE INVENTION

In a first aspect, the present invention provides a crystalline form of compound (I),

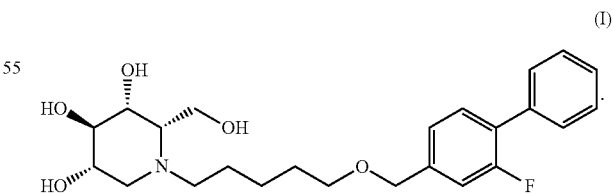

(I)

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a further aspect, the present invention provides a pharmaceutical composition comprising the crystalline form of compound (I) as described herein.

In a further aspect, the present invention provides the crystalline form of compound (I) as described herein, or the pharmaceutical composition as described herein, for use in therapy.

In a further aspect, the present invention provides the crystalline form of compound (I) as described herein, or the pharmaceutical composition as described herein, for use as a medicament.

Another aspect of the present invention relates to the crystalline form of compound (I) as described herein, or the pharmaceutical composition as described herein, for use in treating a disease involving abnormal levels of glucosylceramide and/or higher levels of glycosphingolipids.

In a further aspect, the present invention provides the crystalline form of compound (I) as described herein, or the pharmaceutical composition as described herein, for use in treating Niemann-Pick type C disease.

In a further aspect, the present invention provides a method of treating a disease involving abnormal levels of glucosylceramide and/or higher levels of glycosphingolipids in human or animal patients comprising administering to a patient in need thereof a therapeutically effective amount of the crystalline form of compound (I) as described herein, or the pharmaceutical composition as described herein.

In a further aspect, the present invention provides a method of treating Niemann-Pick type C disease in human or animal patients comprising administering to a patient in need thereof a therapeutically effective amount of the crystalline form of compound (I) as described herein, or the pharmaceutical composition as described herein.

In a further aspect, the present invention provides a process of preparing the crystalline form of compound (I) as described herein, comprising contacting a sample of compound (I) with a solvent.

In a further aspect, the present invention provides a crystalline form of compound (I) obtained by performing the process as described herein.

In a further aspect, the present invention provides a use of the free base of compound (I) to prepare the crystalline form of compound (I).

In a further aspect, the present invention provides a process of preparing the crystalline form of compound (I) comprising crystallising the free base of compound (I).

In a further aspect, the present invention provides a crystalline form of compound (I) obtained by the process of preparing a crystalline form of compound (I) comprising crystallising the free base of compound (I).

Other preferred embodiments of the compounds according to the invention appear throughout the specification and in particular in the examples.

The present inventors have surprisingly discovered a crystalline form of compound (I) that is stable and non-deliquescent. The present invention has additional advantageous properties, such as a substantial lack of hygroscopicity and a relatively high melting point.

Unexpectedly, the present inventors have additionally discovered a crystalline form of compound (I) which shows good solubility in water. These properties make the crystalline forms of the present invention particularly suitable for use in a pharmaceutical composition.

Crystallization of therapeutic compounds often involves the use of different salts. Typically, salts readily undergo crystallization, and the resulting material facilitates subsequent crystallization of the therapeutic compounds. For this reason, the use of a salt is often the preferred method for crystalizing a therapeutic compound. It is, therefore, surprising that the present inventors have discovered a crystalline free base form of compound (I).

Since the crystalline free base form of any therapeutic compound does not require the presence of a counterion, the concentration of a therapeutic compound in a free base crystalline form powder is usually higher than in the corresponding salt form, which is highly beneficial as it reduces the cost of manufacturing the therapeutic compound.

Without wishing to be bound by theory, it is thought that the crystalline forms of the present invention tend to show the advantageous effects discussed above due to their crystal structure.

BRIEF DESCRIPTION OF THE DRAWINGS

These and other aspects of the invention will now be described with reference to the accompanying Figures, in which:

FIG. 7 shows an overlay of the X-ray powder diffraction patterns of two crystalline forms of compound (I) obtained by equilibration with acetonitrile:
1) Form 3 (Example 3), and
2) Form 2 (Example 2).

FIG. 13 shows scoring of clinical signs from PND 56-70 in NPC (−/−) vehicle and AZ-3102 treated mice.

FIG. 18 shows a template for monitoring Clinical Signs.

DETAILED DESCRIPTION OF THE INVENTION

Figure 1:
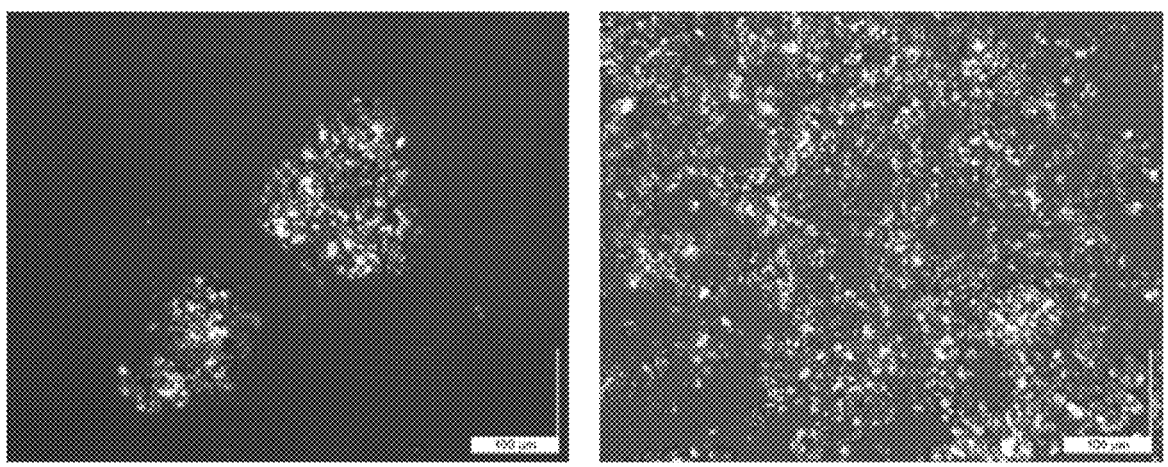
FIG. 1 shows exemplary images obtained using polarized light microscopy of a crystalline form of compound (I), named Form 2, which is obtained by equilibration with acetonitrile; left: as dry powder, right: dispersed in paraffin oil.

Unless otherwise defined herein, scientific, and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

It should be understood that singular prepositions such as "a," "an," and "the," are often used for convenience, however, all instances of the singular are intended to encompass the plural unless otherwise indicated either explicitly or from context. The terms "comprising", "including" and "having" are intended to be inclusive and mean that there may be additional elements other than the listed elements. Further, it should be understood that all references, including journal articles, books, patents, technical documents, and the like, mentioned in this disclosure are hereby incorporated by reference in their entirety and for all purposes.

The term "about" as used herein for numerical data refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a temperature of "about 85° C." can include temperatures between 75° C. and 95° C.

The term "melting point" in the art. The term "relatively high melting point" as used herein is intended to encompass crystalline forms that are stable enough to be formulated as pharmaceutical compositions. Preferably, the term "relatively high melting point" describes a melting point that is greater than about 65° C. More preferably still the melting point is greater than about 80° C.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the crystalline form of compound (I), and optionally the additional ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition comprising a crystalline form of the present invention, and optionally a pharmaceutically acceptable carrier. By "pharmaceutically acceptable" it is meant the carrier, diluent or excipient must be compatible with the other ingredients of the formulation and not deleterious to the recipient thereof.

The term "therapeutically effective amount" means the amount of a crystalline form or a pharmaceutical composition that, when administered to a patient for treating a disease, is sufficient to effect such treatment for the disease. The "therapeutically effective amount" will vary depending on the disease and its severity, and the age and weight of the patient to be treated. The term "patient" (or "subject") includes, but is not limited to, animals such as, for example, mammals. Preferably, the patient is a human.

The present invention provides a crystalline form of compound (I),

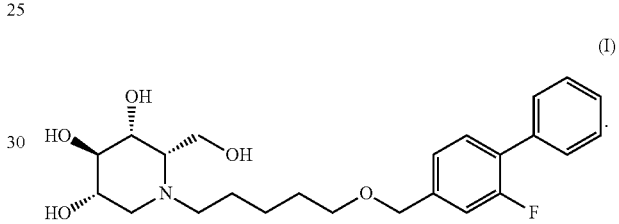

(I)

The crystalline form of compound (I) may be in any crystal state. The crystalline form of compound (I) may be a crystalline salt or a crystalline free base (non-ionized form).

Preferably the crystalline form of compound (I) is a crystalline free base. In addition, compound (I) may form a co-crystal.

If the crystalline form of compound (I) is a crystalline salt, the molecular structure of compound (I) above comprises a protonated nitrogen atom.

The present invention is not limited to a single crystalline form of compound (I). Solid materials may exist in more than one crystalline form. These alternative crystalline forms are termed polymorphs. Each polymorph has different orientations and/or conformations of molecules in the crystal lattice. Each crystal state, or "polymorph", exhibits a unique set of physicochemical properties due to differences in crystal structure.

Polymorphic forms may have different mechanical properties, such as fluidity and compressibility, which affect the technological properties of the compound. Stability and duration of storage of the compound may also depend on the polymorph.

Polymorphs can be distinguished from each other in different ways. Polymorphs clearly exhibit spectroscopic properties, and they can be determined using, for example, infrared spectroscopy, Raman spectroscopy, and $^{13}$C-NMR spectroscopy. In view of the fact that each crystalline form refracts X-rays in different ways, X-ray powder diffraction (XPD) can also be used to characterize polymorphs. In addition, thermal methods such as differential scanning calorimetry (DSC) and thermogravimetric analysis (TTA) can provide unique information on a particular polymorph.

As is well known in the field of powder X-ray diffraction, relative peak heights of powder X-ray diffraction spectra can be used to describe different crystalline forms. Accordingly, in a 'Form 3' aspect, the present invention provides a crystalline form of compound (I) displaying a reflection, stated as a 2Θ value, at 17.8±0.2°, in an X-ray powder diffraction pattern, wherein the reflection at 17.8±0.2° is one of the four strongest reflections in the X-ray powder diffraction pattern. Preferably, the reflection at 17.8±0.2° is one of the three strongest reflections in the X-ray powder diffraction pattern, or wherein the reflection at 17.8±0.2° is one of the two strongest reflections in the X-ray powder diffraction pattern. More preferably, the reflection at 17.8±0.2° is the strongest reflection in the X-ray powder diffraction pattern. More preferably still, in the 'Form 3' aspect, the crystalline form of compound (I) displays a reflection, stated as a 2Θ value, at 17.8±0.1°, in an X-ray powder diffraction pattern, wherein the reflection at 17.8±0.1° is one of the four strongest reflections in the X-ray powder diffraction pattern. Preferably, the reflection at 17.8±0.1° is one of the three strongest reflections in the X-ray powder diffraction pattern, or wherein the reflection at 17.8±0.1° is one of the two strongest reflections in the X-ray powder diffraction pattern. More preferably, the reflection at 17.8±0.1° is the strongest reflection in the X-ray powder diffraction pattern.

Figure 6A:
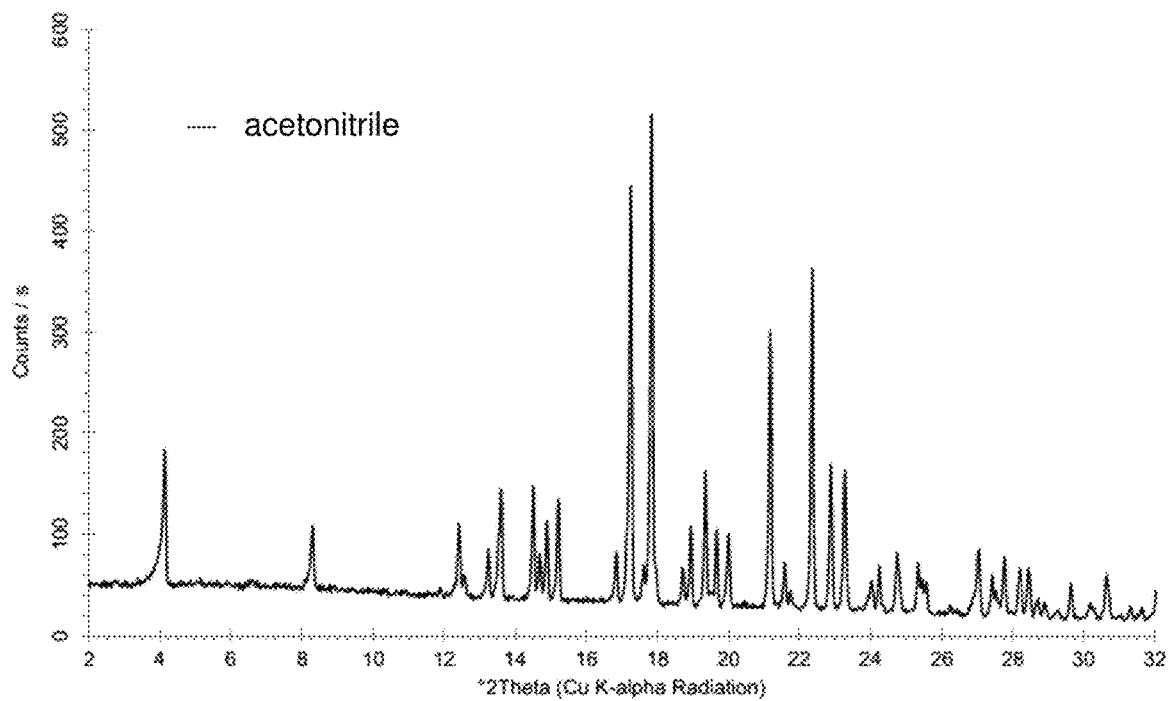
FIG. 6A shows the X-ray powder diffraction pattern of Form 3, obtained by equilibration with acetonitrile.

The term "strongest reflection" describes the highest peak of an X-ray powder diffraction pattern. The height of a peak of a powder X-ray diffraction pattern is determined based on the X-ray intensity (in counts or counts/sec units). Thus, the strongest reflection is a reflection that shows the highest X-ray intensity in the X-ray powder diffraction pattern. For example, the strongest reflection of the X-ray diffraction pattern shown in FIG. 6A is the reflection, stated as a 2Θ value, at 17.8±0.2°.

Unless explicitly stated to the contrary, all X-ray powder diffraction patterns are determined using copper K-alpha radiation at about 25° C.

Preferably, in the 'Form 3' aspect, the crystalline form of compound (I) further displays one or more reflections, stated as a 2Θ value, at one or more of 4.1±0.2°, 8.3±0.2°, 12.4±0.2°, 13.6±0.2°, 14.5±0.2°, 14.9±0.2°, 15.2±0.2°, 17.2±0.2°, 19.3±0.2°, 21.2±0.2°, 22.4±0.2°, 22.9±0.2° and 23.3±0.2°, in an X-ray powder diffraction pattern. More preferably still, in the 'Form 3' aspect, the crystalline form of compound (I) further displays one or more reflections, stated as a 2Θ value, at one or more of 4.1±0.1°, 8.3±0.1°, 12.4±0.1°, 13.6±0.1°, 14.5±0.1°, 14.9±0.1°, 15.2±0.1°, 17.2±0.1°, 19.3±0.1°, 21.2±0.10, 22.4±0.1°, 22.9±0.1° and 23.3±0.1°, in an X-ray powder diffraction pattern.

The positions of peaks of powder X-ray diffraction spectra are relatively insensitive to experimental details. Thus, the crystalline compounds of the invention can be characterized by a powder X-ray diffraction pattern having certain peak positions. Accordingly, in the 'Form 3' aspect, the crystalline form of compound (I) is preferably characterized by reflections, stated as a 2Θ value, at 17.2±0.2°, 17.8 0.2°, 21.2±0.2° and 22.4±0.2°, in an X-ray powder diffraction pattern. More preferably, in the 'Form 3' aspect, the crystalline form of compound (I) is characterized by reflections, stated as a 2Θ value, at 4.1±0.2°, 8.3±0.2°, 12.4±0.2°, 13.6±0.2°, 14.5±0.2°, 14.9±0.1°, 15.2±0.2°, 17.2±0.2°, 17.8±0.2°, 19.3±0.2°, 21.2±0.2°, 22.4±0.2°, 22.9±0.2° and 23.3±0.2°, in an X-ray powder diffraction pattern. More preferably still, in the 'Form 3' aspect, the crystalline form of compound (I) is characterized by reflections, stated as a 2Θ value, at 17.2±0.1°, 17.8 0.1°, 21.2±0.1° and 22.4±0.1°, in an X-ray powder diffraction pattern. Most preferably, in the 'Form 3' aspect, the crystalline form of compound (I) is characterized by reflections, stated as a 2Θ value, at 4.1±0.1°, 8.3±0.1°, 12.4±0.1°, 13.6±0.1°, 14.5±0.1°, 14.9±0.1°, 15.2±0.1°, 17.2±0.1°, 17.8±0.1°, 19.3±0.1°, 21.2±0.1°, 22.4±0.1°, 22.9±0.1° and 23.3±0.1°, in an X-ray powder diffraction pattern.

The crystalline forms of a compound can be characterized by a differential scanning calorimetry (DSC) thermogram. Thus, the crystalline form of compound (I), in the 'Form 3' aspect, is preferably characterized by a DSC thermograph, which shows an onset of endothermic heat flow at about 87° C. and/or a melting point of about 92.4° C., as seen in FIG. 8C. Accordingly, preferably, in the 'Form 3' aspect, the crystalline form of compound (I) has a melting point of 89° C. to 96° C., as determined by DSC. Preferably, the crystalline form, in the 'Form 3' aspect, has a melting point of 90° C. to 95° C., as determined by DSC. More preferably still the crystalline form of compound (I), in the 'Form 3' aspect, has a melting point of 91° C. to 94° C., as determined by DSC. Most preferably the crystalline form of compound (I), in the 'Form 3' aspect, has a melting point of 92° C. to 93° C., as determined by DSC.

The crystalline forms of a compound can be characterized by their hygroscopicity. Hygroscopicity of a product expresses the increase or decrease in its water content as a function of relative humidity at a certain temperature. Substantially non-hygroscopic products exhibit no or only a slight change in their water content as a consequence of variations in relative humidity. In strongly hygroscopic products, water content may vary widely. Accordingly, preferably the crystalline form of compound (I) is substantially non-hygroscopic.

The crystalline forms of a compound can be characterized their thermogravimetric trace. Thus, preferably, the crystalline form of compound (I) can be characterized by its thermogravimetric trace. In one embodiment, the crystalline of compound (I) is characterized by the thermogravimetric trace depicted in FIG. 8A or FIG. 8B.

Figure 9A:
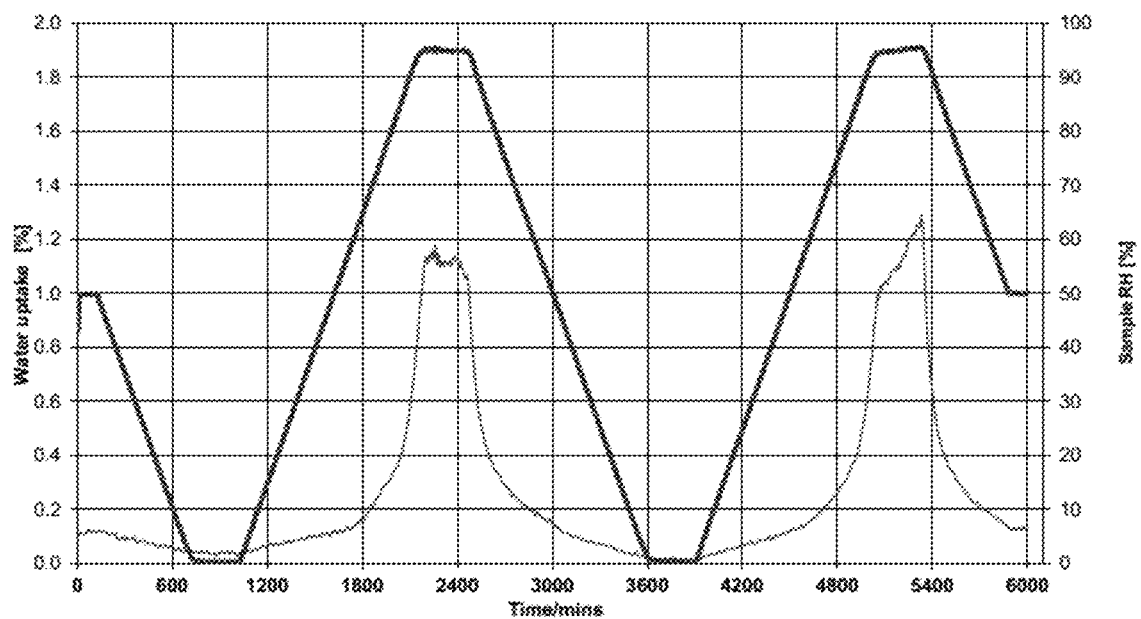
FIG. 9A shows the DVS isotherm of Form 3, obtained by equilibration with ethyl acetate: the change of water content (red curve) and relative humidity (blue curve) as a function of time.
Figure 9B:
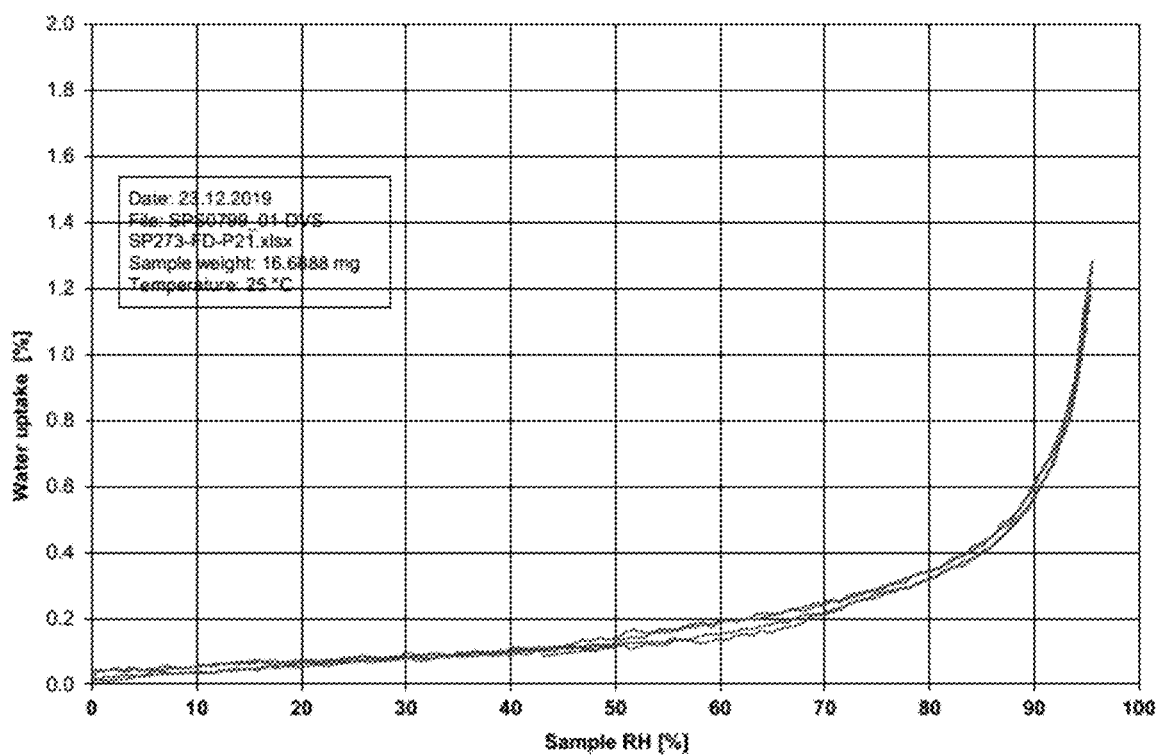
FIG. 9B shows the DVS isotherm of Form 3, obtained by equilibration with ethyl acetate: the change of water content as a function of relative humidity.

The crystalline forms of a compound can also be characterized by their dynamic vapour sorption (DVS) profile. Accordingly, the crystalline form of compound (I) can preferably be characterized by its DVS profile, as seen in FIGS. 9A and 9B. Preferably, the crystalline form of compound (I) has a reversible sorption/desorption profile. Preferably, the DVS profile shows the substantially non-hygroscopic nature of the crystalline form.

Substantially non-hygroscopic substances show a water absorption of less than about 2% at a relative humidity of about 95% measured at a temperature of about 25° C. Preferably, water absorption is less than about 1% at a relative humidity of about 95% measured at a temperature of about 25° C. The values of water absorption are obtained by measuring the mass gain of the tested crystalline form at a relative humidity of about 95% and a temperature of about 25° C. relative to the initial mass.

Accordingly, the crystalline form of compound (I) preferably absorbs 0% to 2% water at a relative humidity of about 95% at a temperature of about 25° C. More preferably still the crystalline form of compound (I) absorbs 0% to 1.5% water at a relative humidity of about 95% at a temperature of about 25° C. Most preferably the crystalline form of compound (I) absorbs 0% to 1% water at a relative humidity of about 95% at a temperature of about 25° C.

Figure 5:
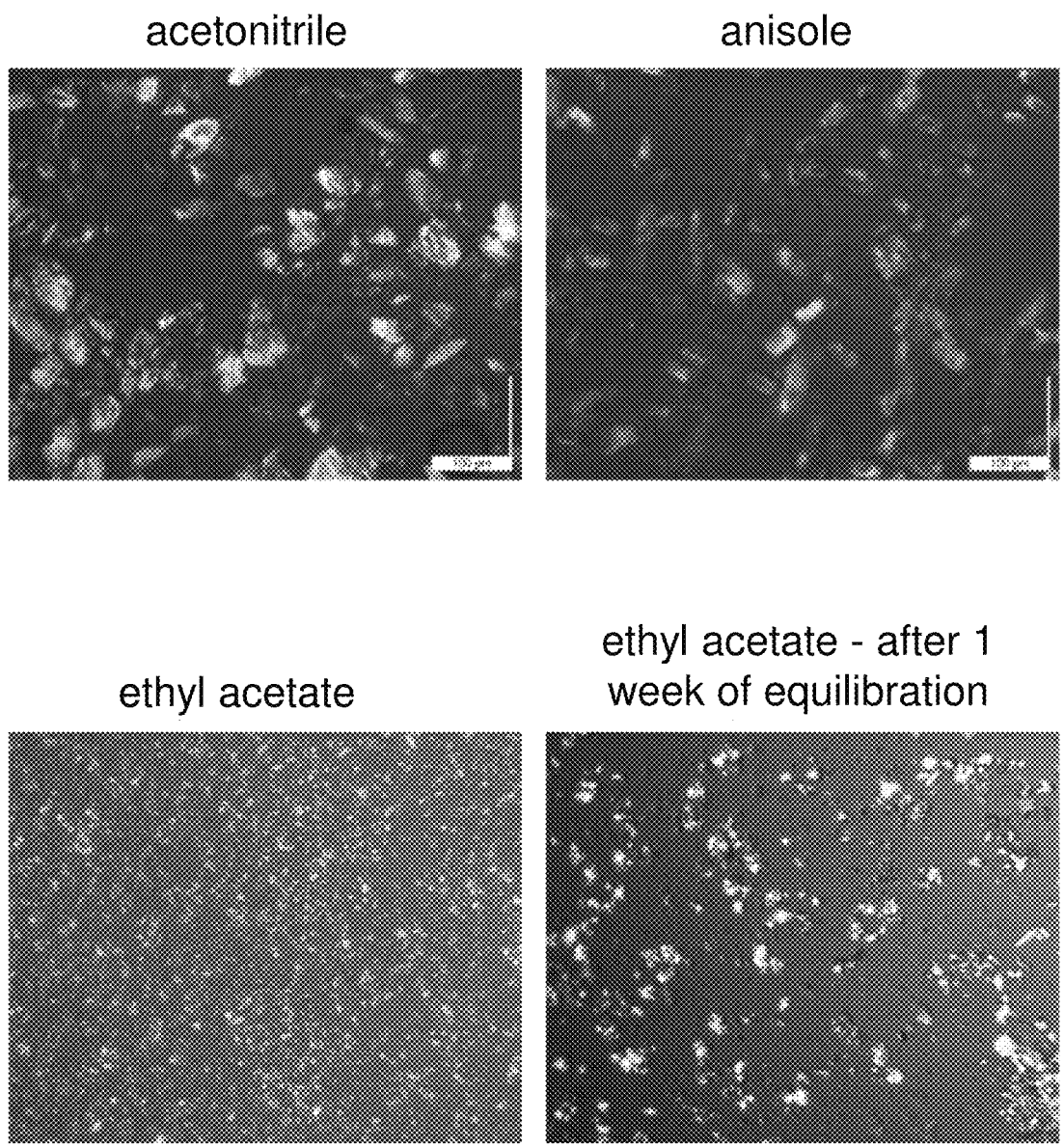
FIG. 5 shows exemplary images obtained using polarized light microscopy of a crystalline form of compound (I), named Form 3, obtained by equilibration with acetonitrile, anisole, or ethyl acetate, respectively.

Additionally, the crystalline form of the present invention is preferably stable. For example, prolonged incubation in ethyl acetate (1 week) at about 25° C. produced crystalline forms of compound (I) of good quality, as shown in FIG. 5.

In a 'Form 2' aspect, the present invention provides a further crystalline form of compound (I). This crystalline form (Form 2) displays a reflection, stated as a 2Θ value, at 16.9±0.2°, in an X-ray powder diffraction pattern, wherein the reflection at 16.9±0.2° is one of the four strongest reflections in the X-ray powder diffraction pattern. Preferably, the reflection at 16.9±0.2° is one of the three strongest reflections in the X-ray powder diffraction pattern, or wherein the reflection at 16.9±0.2° is one of the two strongest reflections in the X-ray powder diffraction pattern. More preferably, the reflection at 16.9±0.2° is the strongest reflection in the X-ray powder diffraction pattern. More preferably still, the crystalline form, in the 'Form 2' aspect, displays a reflection, stated as a 2Θ value, at 16.9±0.1°, in an X-ray powder diffraction pattern, wherein the reflection at 16.9±0.1° is one of the four strongest reflections in the X-ray powder diffraction pattern. Preferably, the reflection at 16.9±0.1° is one of the three strongest reflections in the X-ray powder diffraction pattern, or wherein the reflection at 16.9±0.1° is one of the two strongest reflections in the X-ray powder diffraction pattern. More preferably, the reflection at 16.9±0.1° is the strongest reflection in the X-ray powder diffraction pattern.

Preferably, the crystalline form of compound (I), in the 'Form 2' aspect, displays one or more reflections, stated as a 2Θ value, at one or more of 15.2±0.2°, 16.1±0.2°, 16.5 0.2°, 18.9±0.2°, 23.1±0.2°, 25.5±0.2°, 27.7±0.2° and 28.5±0.2°, in an X-ray powder diffraction pattern. More preferably still, in the 'Form 2' aspect, the crystalline form of compound (I) displays one or more reflections, stated as a 2Θ value, at one or more of 15.2±0.1°, 16.1±0.1°, 16.5±0.1°, 18.9±0.1°, 23.1±0.1°, 25.5±0.1°, 27.7 0.1° and 28.5±0.1°.

This crystalline form of compound (I), in the 'Form 2' aspect, can also be characterized by reflections, stated as a 2Θ value, at 16.1±0.2°, 16.5±0.2°, 16.9±0.2°, 18.9±0.2° and 23.1±0.2°, in an X-ray powder diffraction pattern. Preferably, the crystalline form of compound (I), in the 'Form 2' aspect, can also be characterized by reflections, stated as a 2Θ value, at 16.1±0.1°, 16.5±0.1°, 16.9±0.1°, 18.9±0.1° and 23.1±0.1°, in an X-ray powder diffraction pattern.

Figure 3A:
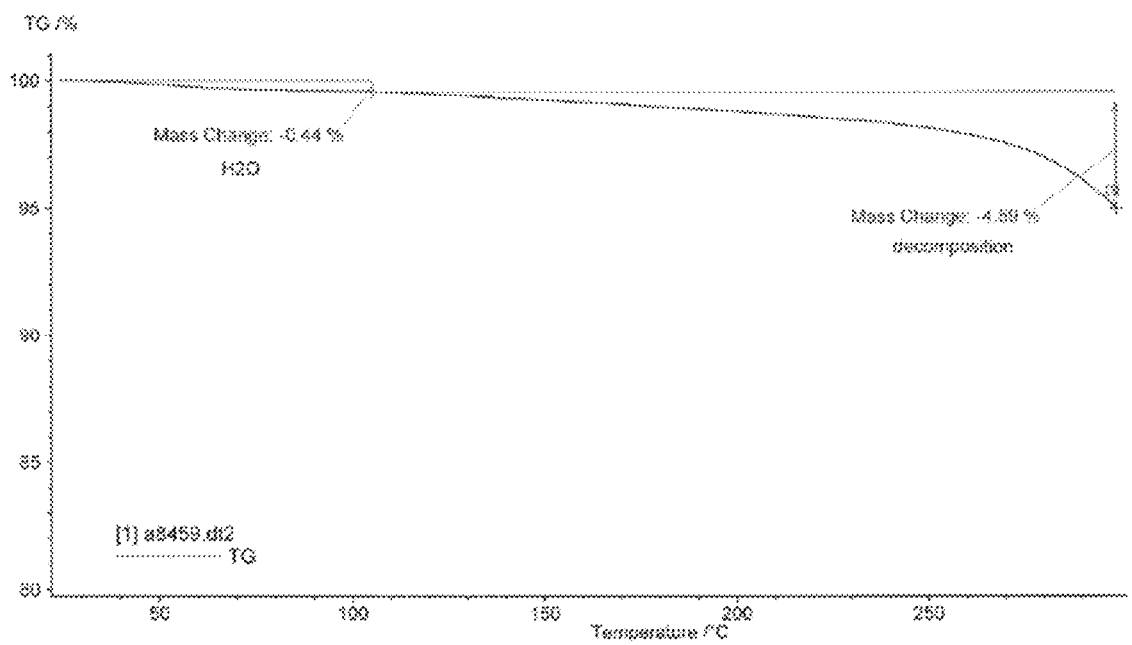
FIG. 3A shows the TG-FTIR thermogram of Form 2, obtained by equilibration with acetonitrile.
Figure 3B:
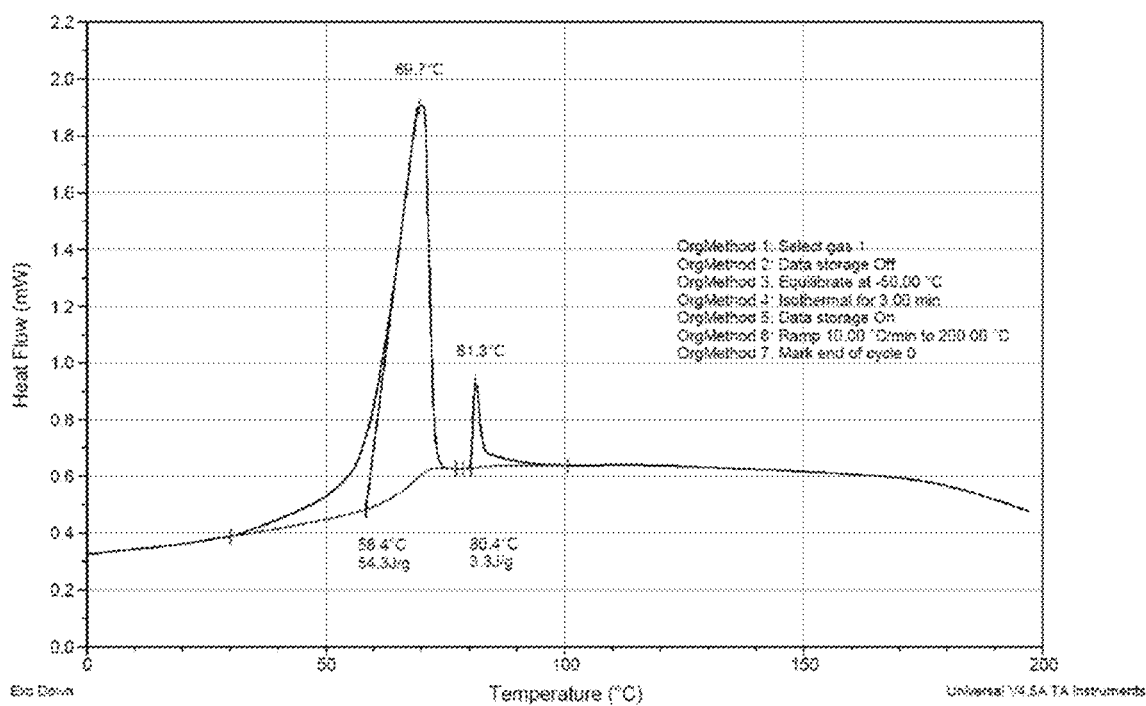
FIG. 3B shows the differential scanning calorimetry (DSC) thermogram of Form 2, obtained by equilibration with acetonitrile.

The crystalline form of compound (I), in the 'Form 2' aspect, can be characterized by a DSC thermograph which shows an onset of endothermic heat flow at about 58° C. and a melting point of about 70° C., as seen in FIG. 3B. Accordingly, the crystalline form of compound (I), in the 'Form 2' aspect, has a melting point of 67° C. to 74° C. Preferably, the crystalline form of compound (I), in the 'Form 2' aspect, has a melting point of 68° C. to 73° C. More preferably still the crystalline form of compound (I), in the 'Form 2' aspect, has a melting point of 69° C. to 72° C. Most preferably the crystalline form of compound (I), in the 'Form 2' aspect, has a melting point of 69° C. to 71° C.

The inventors of the present application have surprisingly discovered that the crystalline form of compound (I), in the 'Form 2' aspect, is particularly soluble in water. Accordingly, preferably the crystalline form of compound (I), in the 'Form 2' aspect, has water solubility of about 75 mg/mL to about 85 mg/mL, measured at about 25° C. More preferably the crystalline form, in the 'Form 2' aspect, has water solubility of about 78 mg/mL to about 82 mg/mL, measured at about 25° C. Most preferably the crystalline form of compound (I), in the 'Form 2' aspect, has water solubility of about 80 mg/mL, measured at about 25° C.

Methods for measuring solubility are known in the art; for example, shake-flask method, sonication, column elution method and ultraviolet or visible spectroscopy method. Unless explicitly stated to the contrary, water solubility is determined using the shake-flask method and/or sonication.

The present invention also provides a pharmaceutical composition comprising the crystalline form of compound (I) as described herein.

Typically, the crystalline form of compound (I) is administered to a patient in the form of a pharmaceutical composition or formulation. Such pharmaceutical compositions may be administered to the patient by any acceptable route of administration including, but not limited to, oral, topical (including transdermal) and parenteral modes of administration.

The pharmaceutical compositions of the invention are typically prepared by pharmaceutically acceptable carrier and one or more optional ingredients. If necessary or desired, the resulting uniformly blended mixture can then be shaped or loaded into tablets, capsules, pills, canisters, cartridges, dispensers, and the like using conventional procedures and equipment.

When intended for oral administration in a solid dosage form (i.e., as capsules, tablets, pills and the like), the pharmaceutical compositions of the invention will typically comprise a crystalline form of compound (I) as the active ingredient. Preferably, the pharmaceutical composition of the invention comprises a crystalline form of compound (I) and no other ingredient. Preferably, the pharmaceutical composition of the invention is contained in a capsule. Preferably, the pharmaceutical composition of the invention is contained in the capsule without any other ingredient. The capsule may be a gelatine capsule or a hydroxypropyl methylcellulose (HPMC) capsule. Alternatively, the pharmaceutical composition of the invention may comprise a crystalline form of compound (I) as the active ingredient and one or more pharmaceutically acceptable carriers. Suitable pharmaceutically acceptable carriers would be known by the person skilled in the art, for example, fats, water, physiological saline, alcohol (e.g., ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

The pharmaceutical composition comprising the crystalline forms of compound (I) can also be administered transdermally or transmucosally using known delivery systems and excipients. For example, the pharmaceutical composition can be admixed with permeation enhancers such as propylene glycol, polyethylene glycol monolaurate, azacycloalkan-2-ones and the like, and incorporated into a patch or similar delivery system. Additional excipients including gelling agents, emulsifiers, and buffers, may also be used.

Injections for parenteral administration include sterile aqueous or non-aqueous solutions, suspensions and emulsions. Aqueous solvents include, for example, distilled water for injection and/or physiological saline. Examples of non-aqueous solvents include alcohols such as ethanol.

Preferably the pharmaceutical composition comprises one or more further pharmaceutically active agents. This combination therapy involves using a crystalline form of compound (I) combined with one or more of the further pharmaceutically active agents, either formulated together (for example, packaged together in a single formulation) or formulated separately (for example, packaged as separate unit dosage forms).

In a healthy individual, the core glycosphingolipid, glucosylceramide, is hydrolysed in lysosomes by acid glucosylceramidase (also called glucocerebrosidase or GBA1, EC 3.2.1.45, UniProt code: P04062). In addition, the non-lysosomal glucosylceramidase (GBA2, UniProt code: Q9HCG7) residing in the cytoplasm is also capable of processing glucosylceramide. As a result, both GBA1 and GBA2 are involved in neuropathological effects observed is several lysosomal storage disorders.

In patients with a lysosomal storage disorder, defects in glycosphingolipid biosynthesis or degradation occur, resulting in abnormal levels of glucosylceramide and/or other glycosphingolipids.

Compound (I) was previously shown (in WO2015/147639 A1) to be effective in the treatment of diseases that are associated with irregular levels of cytosolic or lysosomal glucosylceramide and/or higher levels of glycosphingolipid. As the bioavailability of crystalline forms of compound (I) is comparable to the bioavailability of amorphous compound (I), the crystalline forms of compound (I) are also effective in treating diseases that are associated with abnormal levels of cellular glucosylceramide and/or higher levels of glycosphingolipid. In particular, the crystalline forms of compound (I) are effective in treating diseases that are associated with abnormal levels of cytosolic or lysosomal glucosylceramide and/or higher levels of glycosphingolipid.

As shown in Example 4, the crystalline form of compound (I) (Form 3) is effective in treating diseases that are associated with irregular levels of cytosolic or lysosomal glucosylceramide and/or higher levels of glycosphingolipid. Specifically, Form 3 was shown to improve the clinical signs in Niemann-Pick disease type C mice.

Accordingly, the present invention provides the crystalline form of compound (I) as described herein, or the pharmaceutical composition as described herein, for use in therapy.

The present invention also provides the crystalline form as described herein, or the pharmaceutical composition as described herein, for use as a medicament.

Preferably, the present invention provides the crystalline form of compound (I) as described herein, or the pharmaceutical composition as described herein, for use in treating a disease involving abnormal levels of glucosylceramide and/or higher levels of glycosphingolipids.

Preferably, the disease involving abnormal levels of glucosylceramide and/or higher levels of glycosphingolipids is a lysosomal storage disease, such as Gaucher disease (type 1, 2 and 3), Fabry disease, GM1 gangliosidoses, GM2 gangliosidoses (such as Tay-Sachs disease, Sandhoff disease and the AB variant), Sialidosis, Niemann-Pick disease type C and Action Myoclonus Renal Failure syndrome, or a symptom of one of the diseases collectively classed as metabolic syndrome, such as obesity, insulin resistance, hyperlipidemia, hypercholesterolemia, polycystic kidney disease, type II diabetes and chronic inflammation, or a neurodegenerative disorder, such as Parkinson disease or Lewy-body dementia, or atherosclerosis. More preferably still the crystalline form of compound (I), or the pharmaceutical composition comprising the crystalline form of compound (I) are useful in treating GM1 gangliosidoses and/or GM2 gangliosidoses (such as Tay-Sachs disease, Sandhoff disease and the AB variant).

More preferably still, the present invention provides the crystalline form of compound (I) as described herein, or the pharmaceutical composition as described herein, for use in treating Niemann-Pick disease type C.

The present invention provides the crystalline form of compound (I) as described herein, or the pharmaceutical composition as described herein, for use in treating the Sandhoff disease.

The present invention provides a method of treating a disease involving abnormal levels of glucosylceramide and/or higher levels of glycosphingolipids in human or animal patients comprising administering to a patient in need thereof a therapeutically effective amount of the crystalline form of compound (I) as described herein, or the pharmaceutical composition as described herein.

The present invention provides the crystalline form of compound (I) as described herein, or the pharmaceutical composition as described herein, for use in alleviating the symptoms of a disease involving abnormal levels of glucosylceramide and/or higher levels of glycosphingolipids.

More preferably still, the present invention provides the crystalline form of compound (I) as described herein, or the pharmaceutical composition as described herein, for use in alleviating the symptoms of Niemann-Pick disease type C.

The present invention provides the crystalline form of compound (I) as described herein, or the pharmaceutical composition as described herein, for use in alleviating the symptoms of the Sandhoff disease.

The present invention provides a method of alleviating the symptoms of a disease involving abnormal levels of glucosylceramide and/or higher levels of glycosphingolipids in human or animal patients comprising administering to a patient in need thereof a therapeutically effective amount of the crystalline form of compound (I) as described herein, or the pharmaceutical composition as described herein.

The crystalline form of compound (I) (e.g. Form 3) may be used to improve different clinical signs, for example:
1) disease-associated weight loss;
2) tremor; and/or
3) ataxic gait.

As shown in Example 4, the crystalline form of compound (I) (e.g. Form 3) efficiently penetrates to the brain. Thus, the crystalline form of compound (I) (e.g. Form 3) may be used to treat or alleviate a disease or disease symptoms which originate in the brain. For example, the crystalline form of compound (I) (e.g. Form 3) may be used to prevent or reduce the cerebellar Purkinje cell loss. The crystalline form of compound (I) (e.g. Form 3) may be used to prevent or reduce neuronal death. The crystalline form of compound (I) (e.g. Form 3) may be used to prevent or reduce cerebral atrophy.

The high effectiveness of the crystalline form of compound (I) in treating diseases involving abnormal levels of glucosylceramide and/or higher levels of glycosphingolipids is understood to result from high potency of the crystalline form of compound (I) towards glucosylceramide synthase (GCS) and the non-lysosomal glucosylcerebrosidase (GBA2).

The methods described herein may be in vitro methods or in vivo methods.

Administration can be accomplished either by oral administration via tablets, pills, capsules, granules, powders, solutions, and the like, or parenteral administration, such as injections such as intra-articular, intravenous, and intramuscular injections, suppositories, ophthalmic solutions, eye ointments, or agents for external use, such as transdermal liquid preparations, ointments, transdermal patches, transmucosal liquid preparations, transmucosal patches, inhalers, and the like.

In oral administration, the daily dose is generally from about 0.0001 to 10 mg/kg, preferably from 0.001 to 1 mg/kg, or from 0.005 to 5 mg/kg, and more preferably 0.01 to 0.5 mg/kg, per body weight, administered in one portion or in 2 to 4 separate portions. For example, for a human patient of 70 kg, the optimal daily dose for oral administration is about 0.01-30 mg/day. In the case of intravenous administration, the daily dose is suitably administered from about 0.00001 to 10 mg/kg per body weight, once a day or two or more times a day. In addition, a transmucosal agent is administered at a dose from about 0.0001 to 10 mg/kg per body weight, once a day or two or more times a day. The dose is appropriately decided upon in response to the individual case by taking the symptoms, the age, and the gender, and the like into consideration.

Since the potency of the crystalline form of compound (I) in treating a disease involving abnormal levels of glucosylceramide and/or higher levels of glycosphingolipids(e.g. Niemann-Pick disease type C) is very high, and the required dose relatively low, the crystalline form of compound (I) produces less side effects than known compounds for treating such diseases, for example Miglitol (dose 1200 mg/kg/day).

The present invention also provides a process of preparing the crystalline form as described herein, comprising contacting a sample of compound (I) with a solvent. Preferably, the solvent is selected from acetonitrile, ethyl acetate, isopropanol, anisole, water and tert-butyl methyl ether (TBME). More preferably still, the solvent is ethyl acetate, acetonitrile or isopropanol. Preferably, prior to contacting the sample of compound (I) with the solvent, the sample of compound (I) is purified to remove borate esters. Preferably, the sample of compound (I) is purified using chromatography. More preferably still, the sample of compound (I) is purified using a silica gel chromatography column. Additionally, and/or alternatively the sample of compound (I) is purified by distillation with methanol.

The Form 3 crystalline form of compound (I) can be obtained by any one of the following exemplary methods:

1) Stirring a mixture of about 74 mg of compound (1) and 2.0 ml of acetonitrile for three days at a temperature ranging from 20° C. to 30° C., e.g. about 25° C., then filtering to obtain the crystalline form of compound (I);
2) Stirring a mixture of about 74 mg of compound (1) and 2.0 ml of anisole for three days at a temperature ranging from 20° C. to 30° C., e.g. about 25° C., then filtering to obtain the crystalline form of compound (I);
3) Stirring a mixture of about 82 mg of compound (1) and 1.0 ml of ethyl acetate for three days at a temperature ranging from 20° C. to 30° C., e.g. about 25° C., then filtering to obtain the crystalline form of compound (I);
4) Stirring a mixture of about 82 mg of compound (1) and 1.0 ml of isopropanol for three days at a temperature ranging from 20° C. to 30° C., e.g. about 25°, then filtering to obtain the crystalline form of compound (I);
5) Stirring a mixture of about 45 mg of compound (I) and 1.0 ml of water for three days at a temperature ranging from 20° C. to 30° C., e.g. about 25°, then filtering to obtain the crystalline form of compound (I);
6) Stirring a mixture of about 100 mg of compound (1) and 3.0 ml TBME for three days at a temperature ranging from 20° C. to 30° C., e.g. about 25°, then filtering to obtain the crystalline form of compound (I).

Preferably, before mixing compound (I) with the solvent, the sample of compound (I) is purified to remove borate esters. Preferably, the sample of compound (I) is purified using chromatography. More preferably still, the sample of compound (I) is purified using a silica gel chromatography column. Additionally and/or alternatively the sample of compound (I) is purified by distillation with methanol.

Filtering methods are known to a person skilled in the art, and include, but are not limited to, paper filtering and sintered glass filtering.

The methods of production of Form 3 of compound (I) described herein can be performed on a larger scale maintaining a similar ratio of reagents used. For example, the Form 3 crystalline form of compound (I) can be obtained by stirring a mixture of compound (I) with ethyl acetate in a ratio of between 0.05-1 g to 1 mL [compound (I) to ethyl acetate] for three days at a temperature ranging from 20° C. to 30° C., e.g. about 25° C., then filtering to obtain the crystalline form of compound (I).

The methods for obtaining Form 3 of compound (I) described herein are very efficient. The yield of the methods described herein is typically greater than 70% (as a weight ratio of the amount of Form 3 obtained to the amount of compound (I) initially used). Preferably, the yield of the methods described herein is greater than 75%.

Preferably, the Form 2 crystalline form, is formed as an intermediate, prior to formation of the Form 3 crystalline form.

Preferably the Form 2 crystalline form characterized by reflections, stated as a 2Θ value, at 16.1±0.2°, 16.5±0.2°, 16.9±0.2°, 18.9±0.2° and 23.1±0.2°, in an X-ray powder diffraction pattern is formed as an intermediate, prior to formation of the Form 3 crystalline form characterized by reflections, stated as a 2Θ value, at 17.2 0.2°, 17.8±0.2°, 21.2±0.2° and 22.4±0.2°, in an X-ray powder diffraction pattern.

The present invention also provides a crystalline form of compound (I) obtained by performing the process as described herein.

The present invention also provides the use of the free base of compound (I) to prepare a crystalline form of compound (I).

The present invention also provides a process of preparing the crystalline form of compound (I) comprising crystallising the free base of compound (I).

The present invention also provides a crystalline form of compound (I) obtained by the process of preparing the crystalline form of compound (I) comprising crystallising the free base of compound (I).

Among other advantages, it is thought that forming a crystalline form of compound (I) is useful for purifying compound (I). For example, the crystalline form of compound (I) obtained by the methods described herein has a purity greater than 90%, and typically greater than 95%.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention is further disclosed in the following clauses:

1. A crystalline form of compound (I),

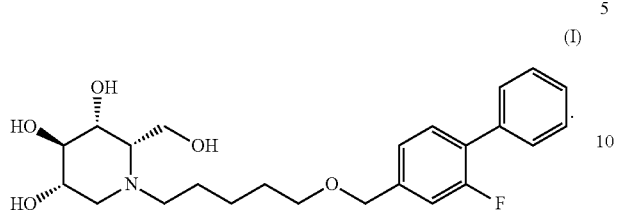

2. The crystalline form of clause 1, wherein the crystalline form is a crystalline free base.
3. The crystalline form of clause 1 or clause 2, wherein the crystalline form displays a reflection, stated as a 2Θ value, at 17.8±0.2°, in an X-ray powder diffraction pattern, wherein the reflection at 17.8±0.2° is one of the four strongest reflections in the X-ray powder diffraction pattern.
4. The crystalline form of clause 3, further displaying one or more reflections, stated as a 2Θ value, at one or more of 4.1±0.2°, 8.3±0.2°, 12.4±0.2°, 13.6±0.2°, 14.5±0.2°, 14.9±0.2°, 15.2±0.2°, 17.2 0.2°, 19.3±0.2°, 21.2±0.2°, 22.4 0.2°, 22.9±0.2° and 23.3±0.2°, in an X-ray powder diffraction pattern.
5. The crystalline form of any one of clauses 1-4, characterized by reflections, stated as a 2Θ value, at 17.2±0.2°, 17.8±0.2°, 21.2±0.2° and 22.4±0.2°, in an X-ray powder diffraction pattern.
6. The crystalline form of any one of clauses 1-5, having a melting point of 89° C. to 96° C.
7. The crystalline form of any one of clauses 1-6, having a melting point of 92° C. to 93° C.
8. The crystalline form of any one of clauses 1-7, wherein the crystalline form is substantially non-hygroscopic.
9. The crystalline form of clause 1 or clause 2, wherein the crystalline form displays a reflection, stated as a 2Θ value, at 16.9±0.2°, in an X-ray powder diffraction pattern, wherein the reflection at 16.9±0.2° is one of the four strongest reflections in the X-ray powder diffraction pattern.
10. The crystalline form of clause 9, further displaying one or more reflections, stated as a 2Θ value, at one or more of 15.2±0.2°, 16.1±0.2°, 16.5±0.2°, 18.9 0.2°, 23.1±0.2°, 25.5±0.2°, 27.7±0.2° and 28.5±0.2°, in an X-ray powder diffraction pattern.
11. The crystalline form of any one of clauses 1, 2, 9 or 10 characterized by reflections, stated as a 2Θ value, at 16.1±0.2°, 16.5±0.2°, 16.9±0.2°, 18.9±0.2° and 23.1±0.2°, in an X-ray powder diffraction pattern.
12. The crystalline form of any one of clauses 9-11, having a melting point of 67° C. to 74° C.
13. The crystalline form of any one of clauses 9-12, having a melting point of 69° C. to 71° C.
14. The crystalline form of any one of clauses 9-13, having water solubility of 75 mg/mL to 85 mg/mL.
15. A pharmaceutical composition comprising the crystalline form of any one of clauses 1-14.
16. The pharmaceutical composition of clause 15, wherein the pharmaceutical composition is contained in a capsule.
17. The pharmaceutical composition of clause 16, wherein the pharmaceutical composition is contained in the capsule without any other ingredient.
18. The pharmaceutical composition of clause 15 or clause 16, comprising at least one pharmaceutically acceptable carrier.
19. The crystalline form of any one of clauses 1-14, or the pharmaceutical composition of any one of clauses 15-18, for use in therapy.
20. The crystalline form of any one of clauses 1-14, or the pharmaceutical composition of any one of clauses 15-18, for use as a medicament.
21. The crystalline form of any one of clauses 1-14, or the pharmaceutical composition of any one of clauses 15-18, for use in treating a disease involving abnormal levels of glucosylceramide and/or higher levels of glycosphingolipids.
22. The crystalline form or the pharmaceutical composition for use of clause 21, wherein the disease involving abnormal levels of glucosylceramide and/or higher levels of glycosphingolipids is a lysosomal storage disease, such as Gaucher disease, Fabry disease, GM1 gangliosidoses, GM2 gangliosidoses (such as Tay-Sachs disease, Sandhoff disease and the AB variant), Sialidosis, Niemann-Pick disease type C and Action Myoclonus Renal Failure syndrome, or a symptom of one of the diseases collectively classed as metabolic syndrome, such as obesity, insulin resistance, hyperlipidemia, hypercholesterolemia, polycystic kidney disease, type II diabetes and chronic inflammation, or a neurodegenerative disorder, such as Parkinson disease or Lewy-body dementia, or atherosclerosis.
23. The crystalline form or the pharmaceutical composition for use of clause 21 or clause 22, wherein the disease is GM1 gangliosidoses or GM2 gangliosidoses (such as Tay-Sachs disease, Sandhoff disease or the AB variant).
24. A method of treating a disease involving abnormal levels of glucosylceramide and/or higher levels of glycosphingolipids in human or animal patients comprising administering to a patient in need thereof a therapeutically effective amount of the crystalline form of any one of clauses 1-14, or the pharmaceutical composition of any one of clauses 15-18.
25. A process of preparing the crystalline form of any one of clauses 1-8, comprising contacting a sample of compound (I) with a solvent.
26. The process of clause 25, wherein the solvent is selected from acetonitrile, ethyl acetate, isopropanol, anisole, water and tert-butyl methyl ether (TBME).
27. The process of clause 25 or clause 26, wherein, prior to contacting the sample of compound (I) with the solvent, the sample of compound (I) is purified.
28. The process of clause 27, wherein the sample of compound (I) is purified using chromatography.
29. The process of clause 28, wherein the sample of compound (I) is purified using silica gel column chromatography.
30. The process of any one of clauses 27-29, wherein, after purification, the sample of compound (I) is free of borate esters.
31. The process of any one of clauses 25-30, wherein the crystalline form of any one of clauses 9-14 is formed as an intermediate, prior to formation of the crystalline form of any one of clauses 1-8.
32. A crystalline form of compound (I) obtained by performing the process of any one of clauses 25-31.
33. Use of the free base of compound (I) to prepare a crystalline form.

34. A process of preparing a crystalline form of compound (I) comprising crystallising the free base of compound (I).
35. A crystalline form of compound (I) obtained by the process of clause 34.
36. A process of preparing a crystalline form of compound (I) comprising the steps of:
   i. adding compound (I) to a purification column to produce a purified sample of compound (I);
   ii. adding a solvent to the purified sample of compound (I) to produce a suspension of compound (I) in the solvent;
   iii. stirring the suspension of compound (I) in the solvent to produce a crystalline form of compound (I); and
   iv. separating the crystalline form of compound (I) to produce a pure sample of crystalline form of compound (I).
37. The process of clause 36, wherein the purified sample of compound (I) is free of borate esters.
38. The process of clause 36 or 37, wherein the solvent is selected from acetonitrile, ethyl acetate, isopropanol, anisole, water and tert-butyl methyl ether (TBME).
39. The process of any one of clauses 36-38, wherein step ii is carried out at a temperature of between 25-35° C.
40. The process of any one of clauses 36-39, wherein stirring in step (iii) is carried out at a temperature of between 20-35° C.
41. The process of any one of clauses 36-40, wherein the stirring in step (iii) is carried out for at least 1 hour.
42. The process of clause 41, wherein the stirring in step (iii) is carried out for at least 16 hours.

EXPERIMENTAL SECTION

Differential scanning calorimetry (DSC) was carried out with a TA Instruments Q2000 instrument (closed aluminum sample pan or aluminum sample pan with a pinhole in the lid, heating rate 20 K/min). The melting point is understood as the peak maximum.

Dynamic vapour sorption (DVS) measurements were performed with an SPS11-100n "Sorptions Prüfsystem" from ProUmid (formerly "Projekt Messtechnik"), August-Nagel-Str. 23, 89079 Ulm (Germany). About 5 mg to 20 mg of sample was put into an aluminum sample pan. Humidity change rates of 5% per hour were used. The applied measurement program can be described as follows:

The sample was placed on an aluminium or platinum holder on top of a microbalance and allowed to equilibrate at a relative humidity (RH) of 50% before starting the pre-defined humidity programs:
   (1) 2 h at 50% RH
   (2) 50→0% RH (5%/h); 5 h at 0% RH
   (3) 0→95% RH (5%/h); 5 h at 95% RH
   (4) 95→0% RH (5%/h); 5 h at 0% RH
   (5) 0→95% RH (5%/h); 5 h at 95% RH
   (6) 95→50% RH (5%/h); 2 h at 50% RH Powder X-ray diffraction was carried out with a Stoe Stadi P diffractometer equipped with a Mythen1 K detector operating with Cu-K$\alpha_1$ radiation. The measurements with this instrument were performed in transmission at a tube voltage of 40 kV and 40 mA tube power. A curved Ge monochromator allows testing with Cu—K $\alpha_1$ radiation. The following parameters were set: 0.02° 2θ step size, 12 s step time, 1.5-50.5° 2θ scanning range, and 1° 2θ detector step (detector mode in step scan). For a typical sample preparation about 10 mg of sample was placed between two acetate foils and mounted into a Stoe transmission sample holder. The sample was rotated during the measurement. All sample preparation and measurement was done in an ambient air atmosphere (about 25° C.).

Approximate solubilities were determined by incremental addition of solvent to about 10 mg the compound and subsequent shaking and/or sonication for a short period of time. If the substance was not dissolved by addition of a total of at least 10 ml solvent, the solubility is indicated as <1 mg/ml. The experiments were conducted at about 25° C.

Thermogravimetric measurements (TG-FTIR) were carried out with a Netzsch Thermo-Microbalance TG 209 coupled to a Bruker FTIR Spectrometer Vector 22 (sample pans with a pinhole, $N_2$ atmosphere, heating rate 10° C./min).

Examples

The following non-limiting examples further illustrate the present invention.

Example 1—Crystalline Salt Formation

A high-throughput salt screening program for compound (I) was carried out with 16 different salt formers identified in Table 1 under six different conditions in the attempt to obtain a crystalline form of compound (I).

The initial screening experiments were carried out by adding a 0.05 M solution of compound (I) in acetone into each well of a quartz 96-microtiter plate followed by the addition of the salt former stock solutions at concentration of 0.1 M. The solvents were evaporated from each well under a flow of nitrogen at room temperature. The solid residues in the wells were investigated by polarized light microscopy.

TABLE 1

Acids selected for the salt screening program

| Salt Former | Molecular Weight | Stahl Class |
| --- | --- | --- |
| Adipic acid | 146.14 | 1 |
| Benzenesulfonic acid | 158.17 | 2 |
| Benzoic acid | 122.12 | 2 |
| Citric acid | 192.12 | 1 |
| Fumaric acid | 116.07 | 1 |
| Gentisic acid | 154.12 | 2 |
| Hydrochloric acid | 36.46 | 1 |
| Lactic acid, L- | 90.08 | 1 |
| Maleic acid | 116.07 | 1 |
| Malic acid, L- | 134.09 | 1 |
| Mandelic acid, DL | 152.15 | 1 |
| Phosphoric acid | 97.99 | 1 |
| Succinic acid | 118.09 | 1 |
| Sulfuric acid | 98.08 | 1 |
| Tartaric acid, L- | 150.09 | 1 |
| Toluenesulfonic acid | 190.22 | 2 |

Although the purpose of this initial experiments was to obtain a 1:1 ratio of compound (I) to a salt former, light microscopy investigations revealed some experimental conditions suitable for crystalline form formation. For example, compound (I) mixed with benzenesulfonic acid, hydrochloric acid, DL-mandelic acid, L-tartaric acid, phosphoric acid and sulfuric acid formed crystalline residues.

In a further screening experiment, six solvent systems were selected, namely acetone, acetonitrile, ethyl acetate, ethanol, an isopropanol-water (3:1) mixture and an acetone/water (9:1) mixture. 200 µL of solvent were added to the residue in each well for slurry equilibrations. The so-prepared microtiter plate was agitated at 400 rpm for one day at room temperature (about 25° C.). Then, the solvents were evaporated under nitrogen flow and the obtained solid residues were investigated by polarized light microscopy.

Based on light microscopy investigations, leads for possible salts were found for benzenesulfonic acid, gentisic acid, hydrochloric acid, L-lactic acid, D-mandelic acid, phosphoric acid, L-tartaric acid and toluenesulfonic acid. Some of the most promising leads were selected for follow up experiments on a scale of 50 to 200 mg (scale up experiments).

The scale up experiments for all tested conditions resulted in the formation of amorphous forms of compound (I) or liquid crystalline salts of compound (I). While the microscopic examination often revealed birefringence, filtration of the obtained mixtures was not possible, and no solid material could be recovered in any of the experiments.

To summarize, all experiments with salt formers failed to produce a crystalline form of compound (I).

Example 2—Form 2 Crystalline Form

As the experiments in Example 1 did not lead to a useful crystalline material, a free base form of compound (I) was investigated.

Compound (I) was purified using a silica gel column to remove borate esters followed by a short equilibration in acetonitrile (about 1-5 min). Solubility of purified compound (I) in acetonitrile was determined to be between 5 mg/mL and 8 mg/mL. Solubility of purified compound (I) in other solvents was also examined and is presented in Table 2. These values were determined by adding small aliquots of solvent to ~10 mg of solid compound (I) and shaking/sonicating for a short period of time at room temperature (about 25° C.).

TABLE 2

Approximate solubility values of purified compound (I).

| Solvent | Solubility S in [mg/ml] |
| --- | --- |
| Acetic acid | S > 120 |
| Acetone | 55 < S < 73 |
| Acetonitrile | 5 < S < 8 |
| DCM | S > 160 |
| Ethanol | 40 < S < 53 |
| Ethyl acetate | 12 < S < 13 |
| MEK | 40 < S < 50 |
| Methanol | S > 160 |
| 1-Propanol | 13 < S < 15 |
| 2-Propanol | 19 < S < 20 |
| THF | S > 200 |
| Water | S~80 |

The Form 2 crystalline form of compound (I) resulting from a short (about 1-5 mins) equilibration in acetonitrile was examined by polarized light microscopy, powder X-ray diffraction (PXRD) experiments, TG-FTIR, differential scanning calorimetry (DSC) and dynamic vapour sorption (DVS).

Figure 2:
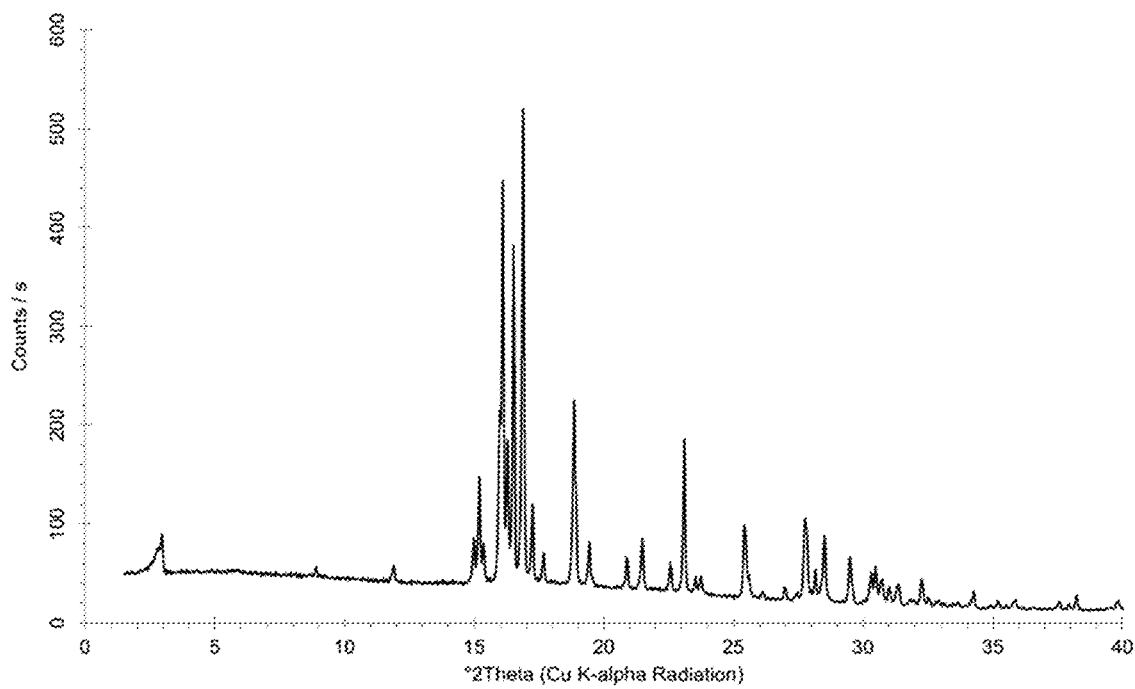
FIG. 2 shows the X-ray powder diffraction pattern of Form 2, obtained by equilibration with acetonitrile.

The results of the polarized light microscopy investigation are presented in FIG. 1, whereas the PXRD pattern is depicted in FIG. 2. This Form 2 crystalline form of compound (I) shows strongest reflections at a 2Θ value of 16.1±0.2°, 16.5±0.2°, 16.9±0.2°, 18.9±0.2° and 23.1±0.2°.

The results of the thermoanalytical characterization of the Form 2 crystalline form of compound (I) obtained from a short equilibration in acetonitrile (TG-FTIR thermogram) are visualised in FIG. 3A, whereas the results for DSC are shown in FIG. 3B. The results reveal that the sample contained about 0.5% of water which is released upon heating to about 120° C. At higher temperatures, thermal decomposition is observed. DSC revealed two significant endothermic events. A first strong endotherm with a peak temperature at about 70° C. and an enthalpy of about 54 J/g is followed by a weaker signal at 81° C. and an enthalpy of about 3 J/g.

Figure 4A:
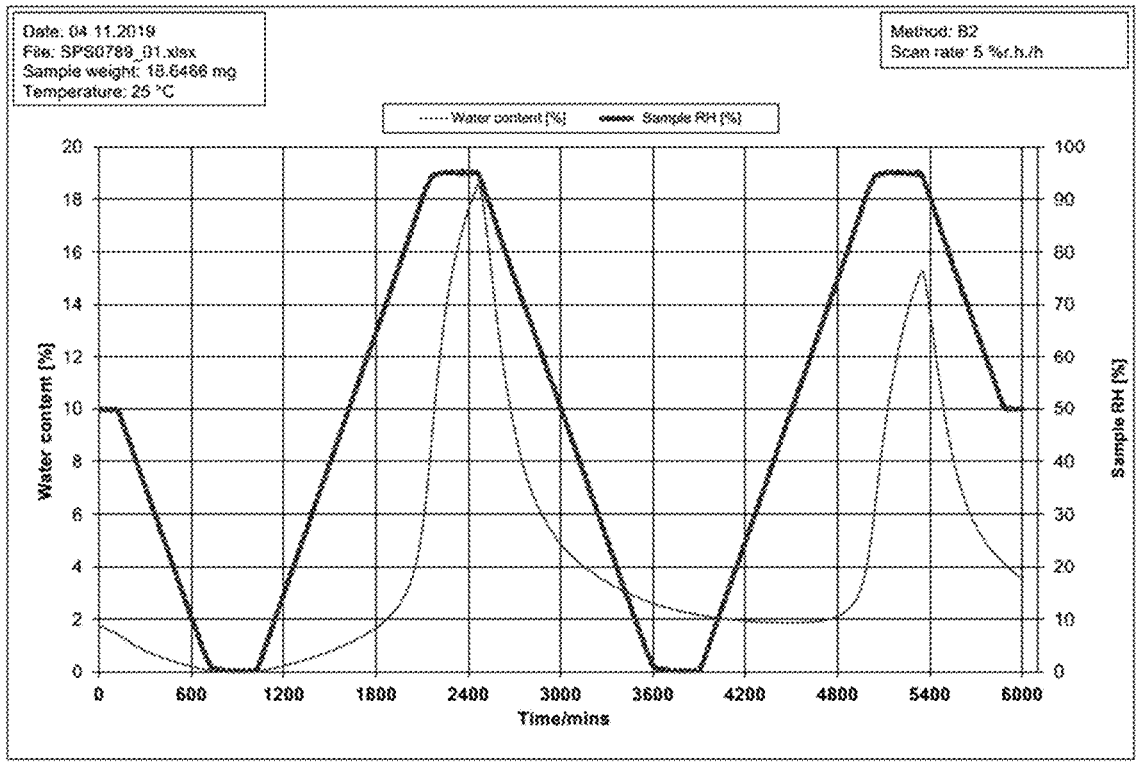
FIG. 4A shows the dynamic vapour sorption (DVS) isotherm of Form 2, obtained by equilibration with acetonitrile: the change of water content (red curve) and relative humidity (blue curve) as a function of time.
Figure 4B:
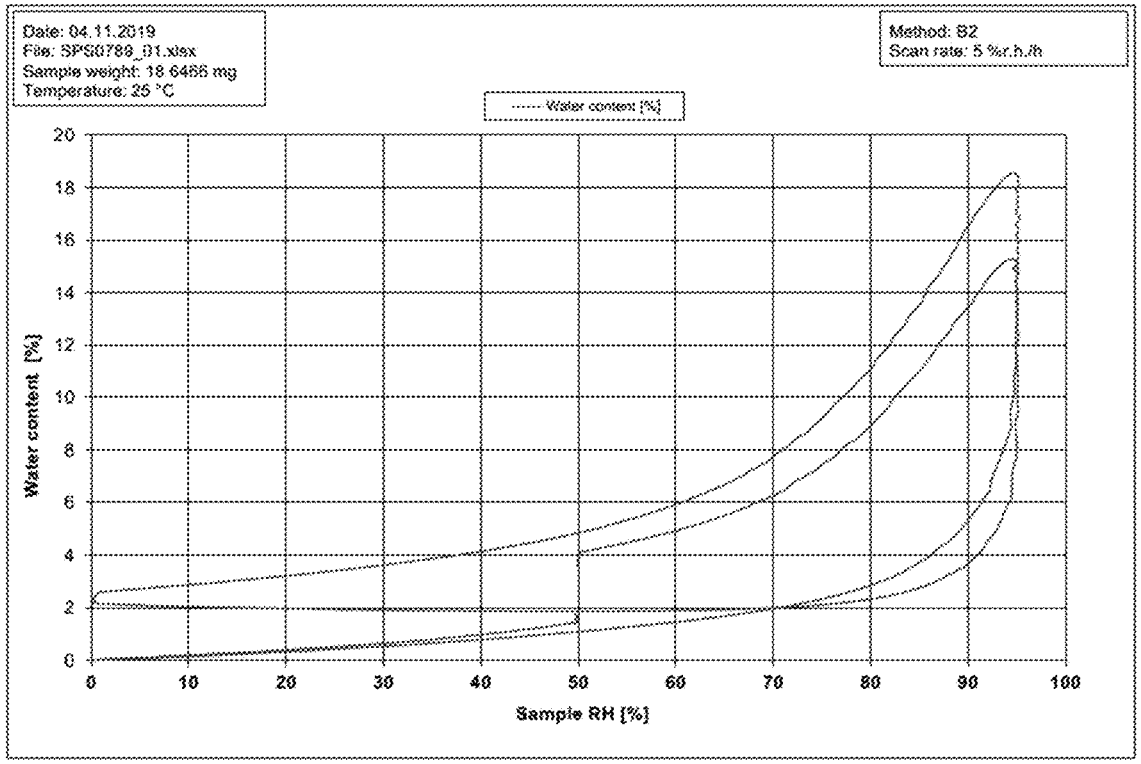
FIG. 4B shows the DVS isotherm of Form 2, obtained by equilibration with acetonitrile: the change of water content as a function of relative humidity.

In addition, the behaviour of the crystalline free base sample was investigated under variable water vapour pressures. At high relative humidity the sample absorbed about 18% of water; however, most of the absorbed water was released when the relative humidity was returned to the 50% RH. The results from the DVS measurement are presented in FIGS. 4A and 4B.

A summary of characteristics of the crystalline form of compound (I) obtained as part of Example 2 is provided in Table 3.

TABLE 3

A summary of characteristics of the Form 2 crystalline form of compound (I).

| Characteristic | Value/description |
| --- | --- |
| Melting point | ~70° C. |
| Hygroscopicity | 18% at 95% RH; hygroscopic |
| Solubility in water | ~80 mg/mL |

The obtained Form 2 crystalline form of compound (I) had a low stability and transitioned into a further Form 3 crystalline form of compound (I) upon exposure to increased temperature (above around 30° C.) for about 1-5 min. Alternatively, Form 2 transitioned into Form 3 upon equilibration in solvent (e.g. acetone) for more than 5 min at around 25° C. This further free base Form 3 crystalline form of compound (I) had a better stability and a unique set of physicochemical properties.

Example 3—Form 3

Independently, a stable crystalline form of compound (I) was obtained from suspension equilibration experiments of purified compound (I) in various respective solvents, for instance, in acetonitrile, ethyl acetate, isopropanol, anisole, water, or TBME respectively, at room temperature (around 25° C.).

In particular a Form 3 crystalline form of compound (I) was obtained by the following experimental methods:
1) about 74 mg of compound (I) was added to 2.0 ml of acetonitrile and the suspension was stirred for three days at room temperature (about 25° C.), then filtered;
2) about 74 mg of compound (I) was added to 2.0 ml of anisole and the suspension was stirred for three days at room temperature (about 25° C.), then filtered;
3) about 82 mg of compound (I) was added to 1.0 ml of ethyl acetate and the suspension was stirred for three days at room temperature (about 25° C.), then filtered;
4) about 82 mg of compound (I) was added to 1.0 ml of isopropanol and the suspension was stirred for three days at room temperature (about 25° C.), then filtered;
5) about 45 mg of compound (I) was added to 1.0 ml of water and the suspension was stirred for three days at room temperature (about 25° C.), then filtered;
6) about 100 mg of compound (I) was added to 3.0 ml TBME and the suspension was stirred for three days at room temperature (about 25° C.), then filtered.

Compound (I) was purified using a silica gel column prior to the addition of the solvent to remove borate esters.

The crystalline form of compound (I) obtained was characterized by polarized light microscopy, powder X-ray diffraction, TG-FTIR, DSC and DVS.

The results of the polarized light microscopy investigation for selected solvents are presented in FIG. 5.

Figure 6B:
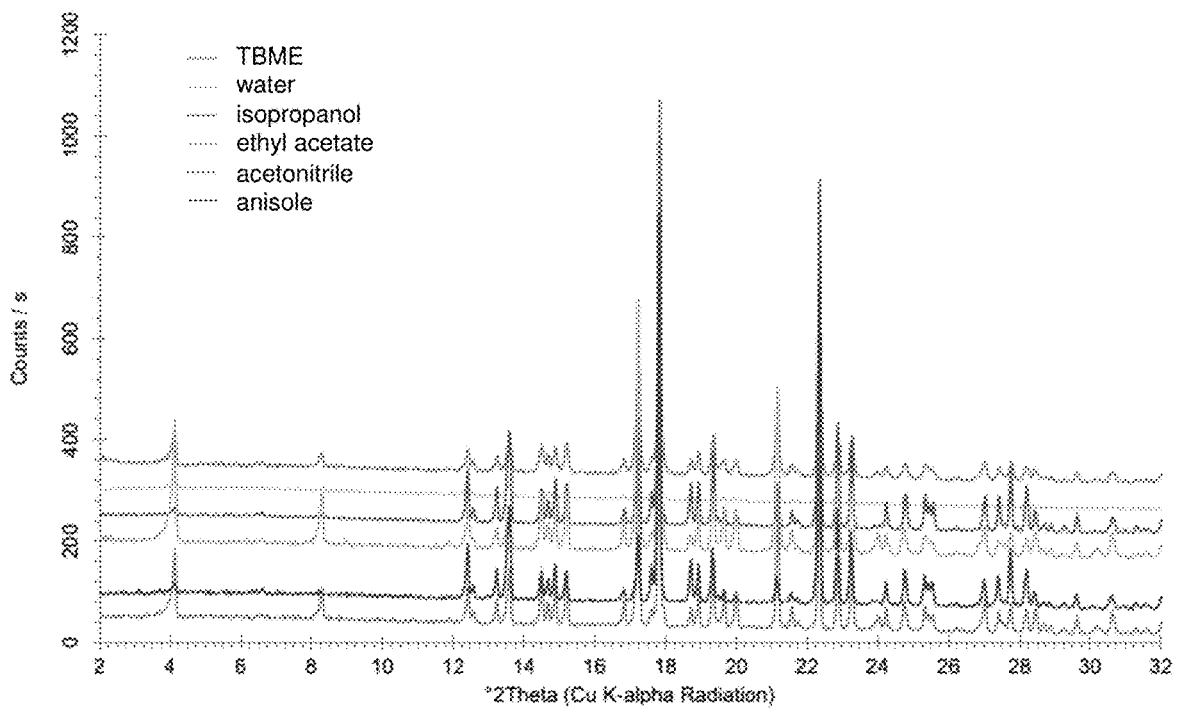
FIG. 6B shows an overlay of the X-ray powder diffraction patterns of Form 3, obtained by equilibration with TBME, water, isopropanol, ethyl acetate, acetonitrile, or anisole, respectively.

The PXRD pattern of the Form 3 crystalline form of compound (I) obtained from suspension equilibration experiments with acetonitrile is shown in FIG. 6A. An overlay of the PXRD patterns of the Form 3 crystalline form of compound (I) obtained from suspension equilibration experiments with other solvents is shown in FIG. 6B. This crystalline form of compound (I) shows strongest reflections at a 2Θ value of 17.2±0.2°, 17.8±0.2°, 21.2±0.2° and 22.4±0.2°. This is consistent despite different solvents being used to obtain the crystalline form of compound (I).

For comparison, FIG. 7 shows an overlay of the PXRD pattern of the crystalline form obtained in Example 2 (Form 2) and the present example (Form 3). The two crystalline forms have a different PXRD pattern.

Figure 8A:
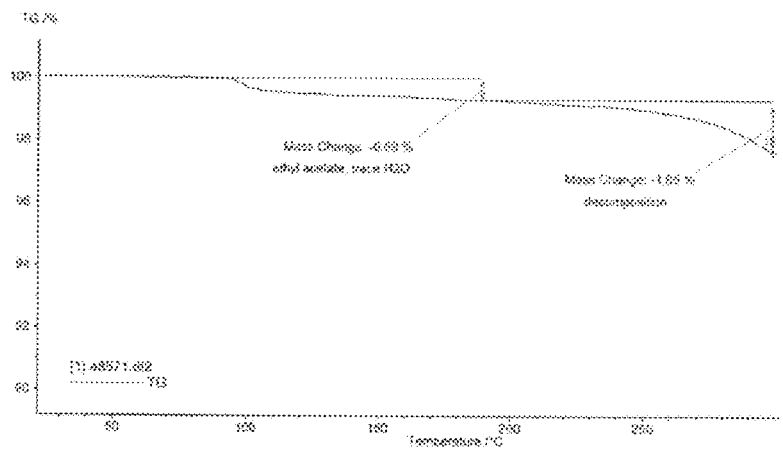
FIG. 8A shows the TG-FTIR thermogram of Form 3, obtained by equilibration with ethyl acetate.

The results of exemplary TG-FTIR characterization experiments of the Form 3 crystalline form of compound (I) are shown in FIGS. 8A (ethyl acetate) and 8B (isopropanol).

FIG. 8A reveals that the sample of the Form 3 crystalline form of compound (I) obtained by equilibration with ethyl acetate contained about 0.7% of ethyl acetate despite drying under vacuum at 40° C. for several days. The ethyl acetate is released between about 100° C. and 200° C. At higher temperatures thermal decomposition is observed.

Figure 8B:
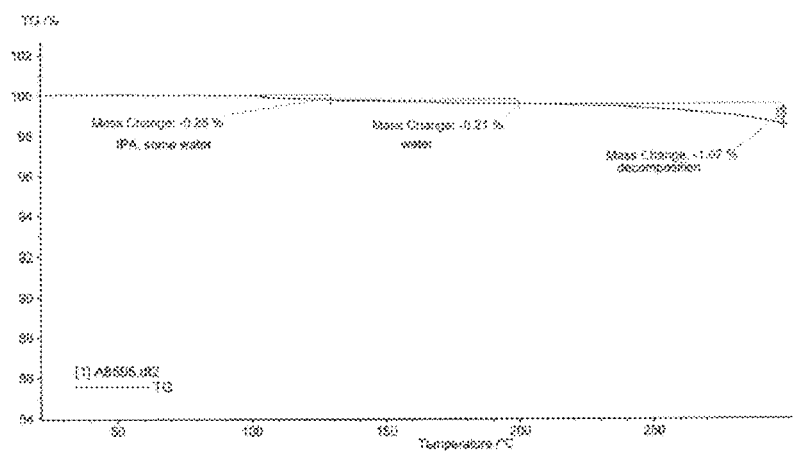
FIG. 8B shows the TG-FTIR thermogram of Form 3, obtained by equilibration with isopropanol.
Figure 8C:
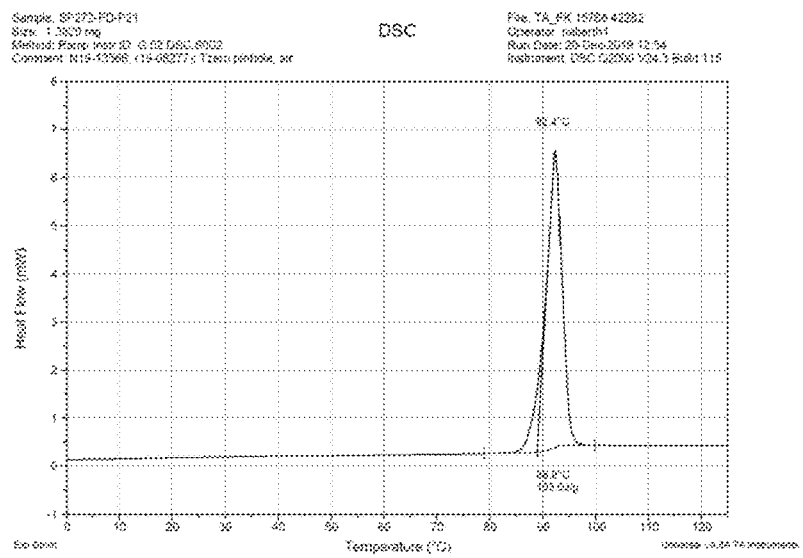
FIG. 8C shows the DSC thermogram of Form 3, obtained by equilibration with ethyl acetate.

The Form 3 sample that resulted from a suspension of compound (I) in isopropanol (and drying in air at room temperature) surprisingly shows that the initial isopropanol content was below 0.5% (see FIG. 8B).

Exemplary DSC measurements for the sample of the Form 3 crystalline form of compound (I) obtained by equilibration with ethyl acetate are depicted in FIG. 8C and show a sharp endothermic melting peak at about 92° C. associated with an enthalpy of about 103 J/g. Thus, the Form 3 crystalline form of compound (I) obtained as part of this Example has a higher melting point than the crystalline form from Example 2 (Form 2).

In addition, the behaviour of the sample of the Form 3 crystalline form of compound (I) obtained by equilibration with ethyl acetate was investigated under variable water vapour pressures. At the highest relative humidity of 95% the sample absorbed about 1.2% of water that was released when the relative humidity was returned to the 50% RH. The results from the DVS measurement are shown in FIGS. 9A and 9B. The amount of absorbed water is small, and the water sorption is reversible. Thus, this Form 3 crystalline form of compound (I) is non-hygroscopic or substantially non-hygroscopic.

A summary of characteristics of the Form 3 crystalline form of compound (I) obtained as part of Example 3 is provided in Table 4.

TABLE 4

A summary of characteristics of a Form 3 crystalline form of compound (I).

| Characteristic | Value/description |
| --- | --- |
| Melting point | ~92.5° C. |
| Hygroscopicity | ~1% at 95% RH; substantially non-hygroscopic |
| Solubility in water | not measured |

Example 4—Effect of Administration of the Crystalline Form of Compound (I) to Mice Suffering from Niemann-Pick Type C (NPC) Disease In the Example, AZ-3102-00 is a name for compound (I) in Form 3.

Aim of the Study

The aim of the study was to evaluate the treatment of young NPC1 (NPC (−/−) mice (P11-P70) with a predicted pharmacologically active dose of AZ-3102-00 using oral gavage, and assess PK and histological markers to characterize neuropathology that may occur.

Study Design

Out of the 38 mice to be included in this study, there were 30 NPC (−/−) knock-out (KO) mice, 4 NPC (+/−) heterozygous mice and 4 NPC (+/+) wild-type (WT, Balb/c) mice. NPC1(−/−) mice have a premature truncation of the protein deleting 11 out of 13 transmembrane domains leaving the first two transmembrane domains intact. NPC1(−/−) mice homozygous for the recessive NIH allele of the Niemann Pick type C1 gene (Npc1 ml N) show a dual deficiency of sphingomyelinase and glucocerebrosidase activity (JAX #003092). Animals were bred on a BALB/c OlaHsd background.

24 NPC1 (−/−) mice were treated per oral gavage with AZ-3102-00 from post-natal day 11 (P11) to post-natal-day 70 (P70). Age-matched control mice included 6 NPC (−/−) and 4 NPC (+/−) mice treated with vehicle, and 4 NPC (+/+) mice received AZ-3102-00. After the last treatment on P70, NPC (−/−) mice (n=4 per timepoint) were euthanized by IP injection of 600 mg/kg pentobarbital at the following timepoints: 30 min, 1 h, 2 h, 4 h, 8 h, and 24 h. Control mice were also sacrificed after the last treatment (not time critical). Terminal blood was collected by heart puncture in EDTA coated tubes. Blood plasma was collected by centrifugation (3000×g for 10 minutes at room temperature) and 50 μL plasma aliquots were transferred to 1.5 mL tubes, frozen on dry ice and stored at −80° C.

After transcardial perfusion, brains were removed and hemisected. Right hemi brains were post-fixed and embedded in cryomolds for further immunohistochemical analysis. Left hemi brains were frozen on dry ice for further analysis.

Brains were cryo-sectioned (12 levels with 5 sections each). 5 Sections per animal were then used for quantitative immunofluorescent labelling of microglia (MAC1) and astrocytes (GFAP) in two brain regions.

Test System and Justification of the Test System

Niemann-Pick type C (NPC) disease is an autosomal recessive neurodegenerative disorder associated with mutations in NPC1 and NPC2 genes and characterized by accumulation of unesterified cholesterol and glycosphingolipids (GSLs). Approximately 95% of Niemann-Pick Type C cases are caused by genetic mutations in the NPC1 gene, referred to as type C1; 5% are caused by mutations in the NPC2 gene, referred to as type C2. The clinical manifestations of Niemann-Pick type C1 and C2 are similar because the respective genes are both involved in egress of lipids, particularly cholesterol, from late endosomes or lysosomes. The NPC1 gene encodes a protein that is located in membranes inside the cell, and is involved in the movement of cholesterol and lipids within cells. A deficiency of this protein leads to the abnormal build-up of lipids and cholesterol within cell membranes. The NPC2 gene encodes a protein that binds and transports cholesterol. Mice homozygous for the recessive NIH allele of the Niemann Pick type C1 gene show a dual deficiency of sphingomyelinase and glucocerebrosidase activity. Mutant mice begin to lose weight and to show tremor and ataxic gait at about 7 weeks of age. Weight loss continues and tremor and ataxia become more severe until death at about 12 to 14 weeks of age. The liver and spleen are also enlarged and Purkinje cells in the cerebellum are severely depleted. Some of these signs in mice resembles that of human Niemann-Pick Type C disease patients.

TABLE 5

Test item information.

| Test item | |
|---|---|
| Name of the T.I. | AZ-3102-00 |
| Lot Number T.I. | CR-20-02149 |
| Brand | Not applicable |
| Stability | Retest date is April 2021 |
| Composition | Not applicable |
| Purity | 99.4% |
| Molecular weight | 433.5 g/mol |
| Expiry date | Retest date is April 2021 |
| Storage condition (formulation) | Storage and Stability in vehicle: stable stored under nitrogen at room temperature protected from light for at least 24 h, stored under nitrogen in a refrigerator (2-8° C.) for at least 8 days and under nitrogen frozen in a freezer ($\leq$-15° C.) for at least 21 days (3 weeks). |
| Vehicle | Acidified water |
| Treatment dosages | 1.5 mg/kg (from P11-P25) and 3 mg/kg (from P26-P70) |
| Administration route and volume | Per oral gavage, 10 mL/kg |
| Treatment frequency | Daily treatment for 60 days |

Compound Preparation:

Dose formulations were divided into aliquots where required to allow to be dispensed on each dosing occasion.

TABLE 6

Formulation information.

| Dose Formulation | Administration Dose Form | Procedure | Frequency of Preparation | Storage Conditions Set to Maintain |
|---|---|---|---|---|
| Test Item | Solution | Formulations (w/w) were prepared by dissolving the test item in Ampuwa water in a nitrogen environment | At least weekly or two times per week if a nitrogen environment could not be used during dissolution | 2-8° C. protected from light |

The required amount of test item was weighed and dissolved in Elix water (w/w) and pH adjusted to an acidic pH. No further excipients were added.

No corrections were made for specific gravity of the test item, or purity/composition of the test item.

After each dose preparation, a retain of the solution were frozen for analysis at the end of the study.

Stability analyses performed previously in conjunction with the method development and validation study demonstrated that the test item is stable in the vehicle when prepared and stored under the same conditions at concentrations bracketing those used in this study for at least 24 hours at room temperature protected from light, for at least 8 days refrigerated (2-8° C.) and for at least 3 weeks in the freezer ($\leq$-15° C.) at concentrations bracketing those used in the present study (0.01 to 2 mg/mL).

Animal Management

Accommodation of Animals

Animals were housed in individual ventilated cages on standardized rodent bedding supplied by Rettenmaier. Each cage contained a maximum of five mice. The temperature in the keeping room was maintained between 20 to 24° C. and the relative humidity was maintained between 45 and 65%. Animals were housed under a constant light-cycle (12 hours light/dark). Dried, pelleted standard rodent chow (Altromin) as well as normal tap water was available to the animals ad libitum. Wet food was supplied to animals upon the attending Veterinarian's guidance.

Identification

Animals were numbered consecutively by classical ear-marking.

Each cage was identified by a coloured card indicating the study number, sex, the individual registration numbers (IRN) of the animals, date of birth, as well as the treatment group allocation. The genotype (transgenic or wild type) of each animal was determined by PCR specific for the transgenic construct. Each mouse was genotyped using DNA isolated from ear biopsy prior to study start.

Group Allocation

Only animals in apparently good health condition were included to the study. Randomization of group allocation was done per cage. Animals were assigned to different starting groups (cohorts) comprising animals of all treatment groups. The number of animals in a starting group was limited to ensure same age and uniform handling.

Health Status and Cage-Side Observations

Before enrolment to the study, the health status of each individual animal was evaluated.

During the study, daily observations were made, and any notable cage-side observations were recorded and immediately reported to the study director and the attending veterinarian, who decided on further actions (e.g., euthanasia).

Body weights and health status were recorded daily for the first week and later once a week.

Premature Termination and Humane Endpoints

No animals had to be prematurely euthanized.

Materials and Methods

Animals

Mouse line: NPC (−/−)

Breeder: QPS Austria GmbH, Grambach, Austria

Age at start: Post-natal day 11 (P11) to post-natal-day 70 (P70)

Sex: Mixed

Number of animals: 30 NPC (−/−), 4 NPC (+/−), 4 NPC (+/+)

Treatment

24 NPC1 (−/−) mice (groups D to I) were treated per oral gavage (10 mL/kg) with AZ-3102-00 from post-natal day 11 (P11) to post-natal-day 70 (P70). Dosing will start at 1.5 mg/kg from P11 to P25, followed by 3 mg/kg from P26 to P70. Control mice included 6 NPC1 (−/−) and 4 NPC (+/−) mice treated with vehicle and 4 NPC (+/+) mice received AZ-3102-00 (groups A to C).

After the last treatment on P70, NPC (−/−) mice (n=4 per timepoint; groups D to I) were euthanized by IP injection of 600 mg/kg pentobarbital a the following timepoints: 30 min, 1 h, 2 h, 4 h, 8 h, and 24 h. Control mice (groups A, B and C) were also sacrificed after the last treatment (not time critical).

TABLE 7

Treatment group overview.

| Group | Animals | Sex | Treatment | Test item | Concentration[a] | n |
|---|---|---|---|---|---|---|
| A | NPC (−/−) | mixed | p.o | Vehicle | N/A | 6 |
| B | NPC (+/−) | mixed | p.o | Vehicle | N/A | 4 |
| C | NPC (+/+) | mixed | p.o | AZ-3102-00 | Dose 1 & 3 mg/kg | 4 |
| D | NPC (−/−) | mixed | p.o | AZ-3102-00 | Dose 1 & 3 mg/kg | 4 |
| E | NPC (−/−) | mixed | p.o | AZ-3102-00 | Dose 1 & 3 mg/kg | 4 |
| F | NPC (−/−) | mixed | p.o | AZ-3102-00 | Dose 1 & 3 mg/kg | 4 |
| G | NPC (−/−) | mixed | p.o | AZ-3102-00 | Dose 1 & 3 mg/kg | 4 |
| H | NPC (−/−) | mixed | p.o | AZ-3102-00 | Dose 1 & 3 mg/kg | 4 |
| I | NPC (−/−) | mixed | p.o | AZ-3102-00 | Dose 1 & 3 mg/kg | 4 |

[a]mice were treated at 1 mg/kg from P11-P25 and then 3 mg/kg from P26-P70

Tissue Sampling

At 30 min (Group D), 1 h (+/−5 min. Group E), 2 h (+/−5 min. Group F), 4 h (+/−5 min. Group G), 8 h (+/−5 min. Group H), and 24 h (+/−5 min. Group 1) (all time critical) after the last treatment on P70, mice were euthanized by i.p. injection.

6 NPC1 (−/−) of group A, 4 NPC (+/−) of group B treated and 4 NPC (+/+) mice of group C served as controls and were also euthanized on P70 (approximately 2 h after the last treatment).

Mice were terminally anesthetized by i.p. injection of Pentobarbital (600 mg/kg, dose 10 μL/gram body weight).

Blood Sampling

The thorax was opened, and blood was collected by heart puncture with a 23-gauge needle.

The needle was removed, and the blood was transferred to the sample tube (MiniCollect® K2EDTA (potassium ethylenediaminetetraacetic acid). The tube was inverted thoroughly to facilitate homogeneous distribution of the EDTA and prevent clotting. The blood samples were centrifuged at 3000×g for 10 minutes at room temperature (22° C.). 50 μL plasma aliquots were transferred to pre-labelled 1.5 ml LoBind Eppendorf tubes, frozen on dry ice and stored at −80° C.

Perfusion

Animals were then transcardially perfused with 0.9% saline. To this end, a 23-gauge needle connected to a bottle with 0.9% saline was inserted into the left ventricle. The thoracic aorta—between the lungs and the liver—was clamped with hemostatic forceps to block the blood flow from the heart to the abdomen but allowing the blood flow to the brain. The right ventricle was opened with scissors. A constant pressure of 100 to 120 mm Hg was maintained on the perfusion solution by connecting the solution bottle to a manometer-controlled air compressor. Perfusion was continued until the skull surface has turned pale and only perfusion solution instead of blood exited of the right ventricle.

Brain Sampling

After perfusion the skull was opened, and the brain was removed carefully and hemisected on a cooled surface. The left hemisphere was weighed, snap frozen on dry ice and stored at −80° C. The right hemisphere was fixed by immersion in 4% paraformaldehyde in phosphate buffer (pH 7.4) for 2 hours at room temperature.

Histology

Tissue Preparation

Mouse right hemi-brains were fixed by immersion in freshly prepared 4% paraformaldehyde in PB (pH 7.4) for two hours at room temperature. Afterwards, hemispheres were transferred to 15% sucrose/PBS and stored at 4° C. until sunk to ensure cryoprotection. Tissue blocks were then trimmed as needed, transferred to cryomolds, embedded in OCT medium, frozen in dry ice-cooled isopentane and stored in an ultra-deep freezer (set at −80° C. target temperature).

Sectioning

Figure 10:
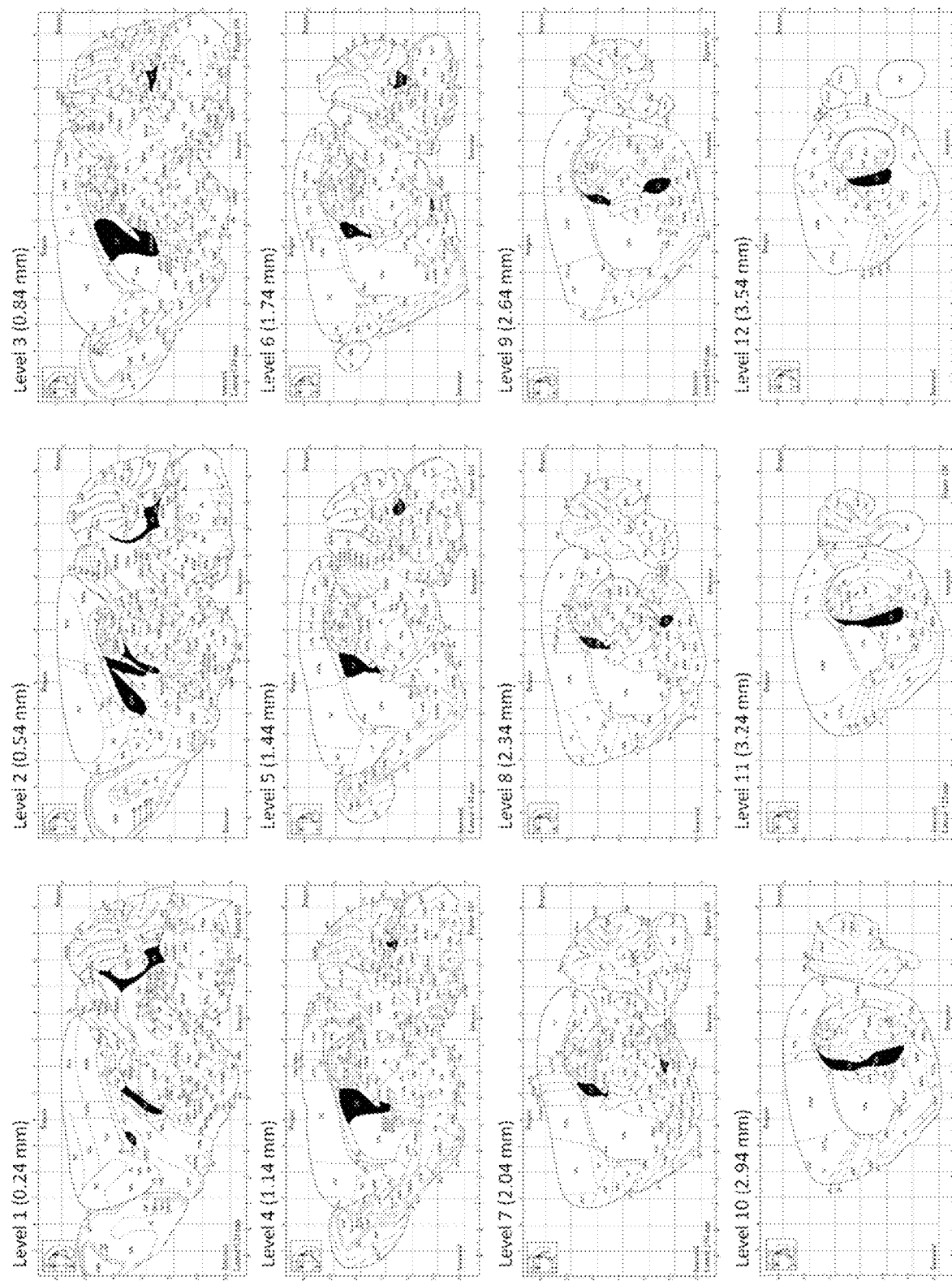
FIG. 10 shows approximate medio-sagittal levels obtained following the sectioning protocol based on Paxinos & Franklin "The Mouse Brain Atlas, 2$^{nd}$ edition", showing the stereotaxic coordinates.
Figure 15:
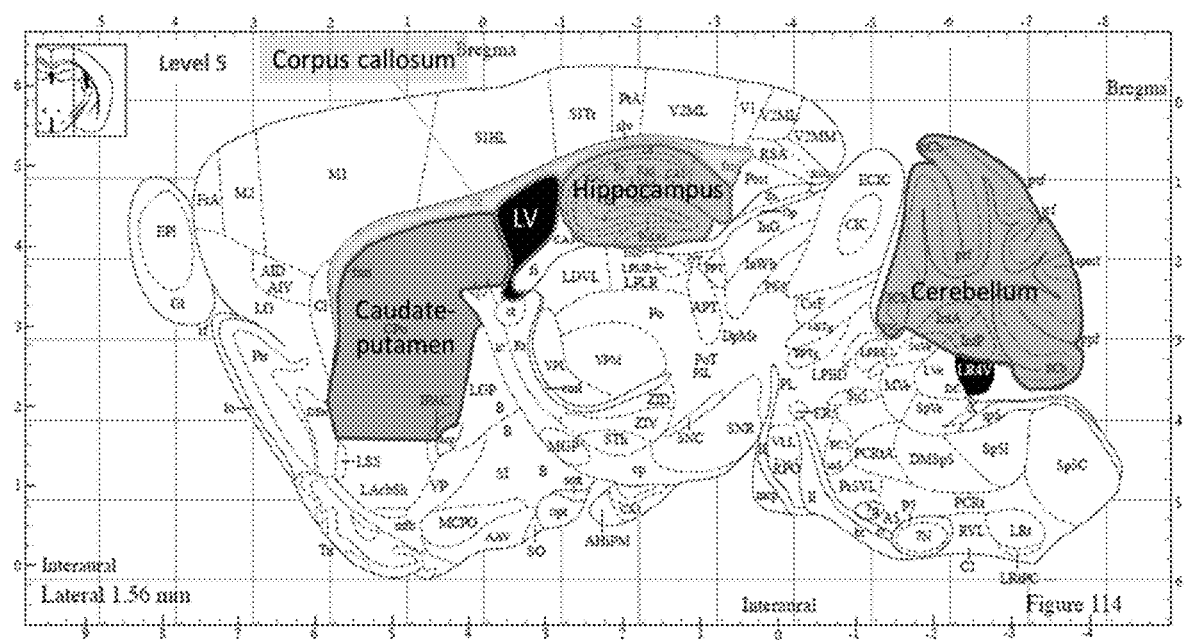
FIG. 15 shows definition of the areas of interest (ROIs). The image shows the outline of the ROIs of the cerebellum, hippocampal formation, corpus callosum, and striatum (caudate-putamen).

Five consecutive cryosections were sagittally cut at 10 μm thickness on a Leica cryotome. The next 25 sections per level were discarded. This collection scheme was repeated for 12 levels and may have been modified to collect from the correct levels, e.g., if brains were smaller due to young age or genotype. In total 12×5=60 sections were collected. Sectioning levels were chosen according to the brain atlas of Paxinos and Franklin ("The Mouse Brain in Stereotaxic Coordinates", $2^{nd}$ edition, 2001). Collection of sections started at a level ~0.2 mm lateral from midline and extend through the hemisphere to ensure systematic random sampling through the target regions (FIGS. 10 and 15). Sections were stored at −20° C. Almost the entire brain was sectioned, so the residual tissue block was disposed when all sections were collected.

Immunofluorescence Exp3531 (Calbindin-D28k)

For each incubation, a uniform systematic random set of five sections per mouse was selected (one section each from levels 2, 4, 6, 8, 10); for information on systematic random sampling follow this link: http://www.stereoloqy.info/sampling/

All steps were executed in Dulbecco's phosphate buffered saline pH 7.2-7.8 (PBS) at room temperature unless noted otherwise.

1. Cryosections were air-dried for 45 minutes and washed in PBS for 10 minutes
2. unspecific binding sites were blocked with 10% normal donkey serum (Jackson Immuno Research) in 0.1% TritonX-100/PBS for 60 minutes in a damp chamber
3. sections were washed 3×5 minutes each in PBS
4. sections were incubated with primary antibodies in 1% normal donkey serum/PBS over night at 4° C. in a damp chamber
   guinea pig polyclonal antibody to Calbindin-D28k (Synaptic Systems, 214005) 1:1000
5. sections were washed 3×5 minutes each in PBS
6. sections were incubated with secondary antibodies in 1% normal donkey serum/PBS for 60 minutes in a damp chamber (light protected)
   donkey anti-guinea pig (H+L), Cy3-conjugated (Jackson ImmunoResearch, 706-165-148), 1:500
7. sections were washed 3×5 minutes each in PBS (light protected)
8. sections were incubated with DAPI working solution for 15 minutes (light protected)

9. sections were washed 2×5 minutes in PBS (light protected)
10. sections were washed 5 minutes in ddH$_2$O (light protected)
11. sections were covered with Mowiol and coverslips (light protected)

Imaging

Whole slide scans of the stained sections were recorded on a Zeiss automatic microscope AxioScan Z1 with high aperture lenses, equipped with a Zeiss Axiocam 506 mono and a Hitachi 3CCD HV-F202SCL camera and Zeiss ZEN 2.3 software.

Quantification

Image analysis was done with Image Pro 10 (Media Cybernetics). At the beginning, the target areas (cerebellum and hippocampus, or corpus callosum and striatum) were identified by drawing regions of interest (ROI) on the images. Additional ROIs exclude wrinkles, air bubbles, or any other artefacts interfering with the measurement. Afterwards, immunofluorescence was quantitatively evaluated within the identified areas.

For quantification we used background correction if necessary and detect immunoreactive objects by adequate thresholding and morphological filtering (size, shape). Different object features were then quantified; among them the percentage of cumulative object area based on ROI size (immunoreactive area; this is the most comprehensive parameter indicating whether there are differences in immunoreactivity), the number of objects normalized to ROI size (object density), the mean signal intensity of identified objects (mean intensity; this indicates if there are differences in the cellular expression level of target proteins), and the size of above-threshold objects. Once the parameters of the targeted objects had been defined in a test run, the quantitative image analysis ran automatically so that the results are operator-independent and fully reproducible.

Raw data was organized and sorted in Excel, and then transferred to GraphPad Prism for statistical analysis and preparation of graphs. Prism graphs are part of the study report and tables with sorted raw data are attached to the final report after quality checks have been executed.

Measurement of AZ-3102 and Glucosylceramide in Mice Plasma and Brain Tissue First, plasma samples were protein precipitated with a solution of acetonitrile/ultrapure water/methanol (90:5:5) containing 500 nM of the internal standard glucosylceramide C17:0 (GlcCer C17:0) and 0.1% formic acid. After 5 min mixing at room temperature, the samples were centrifuged for 5 min (13,000 rpm, 20° C.) and 50 µL of the supernatants were transferred into a siliconized MTP 96-well plate.

Brain tissues were homogenized in a solution of ultrapure water:methanol (1:1) with 0.1% formic acid (4 mL for each gram of tissue) using a FastPrep 24™ Microtube homogenizer. Tissues homogenates were then mixed for protein precipitation with a solution of acetonitrile:ultrapure water:methanol (90:5:5) containing 500 nM of GlcCer C17:0 and 0.1% formic acid. After a 5-min incubation at room temperature, the samples were centrifuged for 5 min (13000 rpm, 20° C.) and 50 µL of the supernatants were transferred into a siliconized MTP 96-well plate.

Measurements of AZ-3102

Plasma samples were first mixed for protein precipitation with a solution of acetonitrile containing 50 ng/mL of AZ-3101 (internal standard). After 5 minutes incubation at room temperature, the samples were centrifuged for 5 minutes (13000 rpm, 4° C.) and the supernatant was diluted 10-fold in ultrapure water with 0.1% formic acid.

Brain tissues were homogenized in a solution of ultrapure water:methanol (1:1) with 0.1% formic acid (4 mL for each gram of tissue) using a FastPrep 24™ Microtube homogenizer (MP Biomedicals, USA). Brain homogenates were mixed for protein precipitation with a solution of acetonitrile containing 10 ng/mL of AZ-3101 (internal standard). After 5 minutes incubation at room temperature, the samples were centrifuged for 5 minutes (13000 rpm, 4° C.) and the supernatant was diluted 10-fold in ultrapure water with 0.1% formic acid.

Diluted plasma and brain tissue supernatants were injected into an Agilent LC system (Agilent, USA) by an automated sample injector (SIL-30, Shimadzu, USA). Analytes were separated by liquid chromatography using a linear gradient of mobile phase B at a flow rate of 0.800 mL/min on a reversed phased XBridge BEH C8 column (2.1*50 mm, 2.5 µm particle size; Waters, USA) held at a temperature of 40° C. Mobile phase A consisted of ultrapure water with 0.1% formic acid. Mobile phase B was acetonitrile with 0.1% formic acid. Acquisitions were achieved in positive ionization mode using an API 5500 triple quadrupole mass spectrometer (AB Sciex, USA) equipped with a Turbo Ion Spray interface. Data were calibrated and quantified using the Analyst™ data system (AB Sciex, version 1.6.3). LLOQ for AZ-3102 was 0.2 ng/mL in plasma samples, and 2 ng/g tissue in brain, respectively.

Measurement of Glucosylceramide

First, plasma samples were protein precipitated with a solution of acetonitrile/ultrapure water/methanol (90:5:5) containing 500 nM of the internal standard glucosylceramide C17:0 (GlcCer C17:0) and 0.1% formic acid. After 5 min mixing at room temperature, the samples were centrifuged for 5 min (13,000 rpm, 20° C.) and 50 µL of the supernatants were transferred into a siliconized MTP 96-well plate.

Brain tissues were homogenized in a solution of ultrapure water:methanol (1:1) with 0.1% formic acid (4 mL for each gram of tissue) using a FastPrep 24™ Microtube homogenizer. Tissues homogenates were then mixed for protein precipitation with a solution of acetonitrile:ultrapure water:methanol (90:5:5) containing 500 nM of GlcCer C17:0 and 0.1% formic acid. After a 5-min incubation at room temperature, the samples were centrifuged for 5 min (13000 rpm, 20° C.) and 50 µL of the supernatants were transferred into a siliconized MTP 96-well plate.

Concentrations of glucosylceramide C16:0 (GlcCer C16:0), glucosylceramide C18:0 (GlcCer C18:0), and glucosylceramide C24:1 (GlcCer C24:1) brain, samples were quantified by HPLC-MS/MS detection in the multiple-reaction-monitoring mode (MRM). Supernatants were analysed by HPLC-MS/MS while using a HALO HILIC column (150*4.6 mm, 2.7 µm) from Advanced Materials Technology for distinguishing between the galactosyl- and -glucosylceramide isomers. MS/MS acquisitions were achieved in positive ionization mode using an API 4000 triple quadrupole (Applied Biosystems, USA) equipped with a Turbo Ion Spray interface. Analysis of GlcCer C16:0 and GlcCer C18:0 was performed using a gradient with mobile phase A: 5 mM Ammonium Acetate in 94.5% acetonitrile 2.5% Methanol, 2.5% ultrapure water and 0.5% formic acid and mobile phase B: ultrapure Water and 0.1% formic acid. The LLOQ in brain samples for GlcCer 16:0, GlcCer 18:0 and GlcCer 24:1 was 25, 1, 250 and 381.5 pmol/g tissue, respectively.

Statistics

Statistical analysis was performed in GraphPad Prism 9. Data are presented as mean±standard error of mean (SEM) or mean+standard error of mean.

In vivo: Differences between groups were tested with the two-way ANOVA for repeated measurements followed by Bonferroni's or Dunnett's post-hoc analysis.

Histology: Due to low n, distribution of data could not be tested, so normal distribution was assumed. Differences between groups were tested with one-way ANOVA followed by Dunnett's post hoc analysis. Group A (NPC−/−, vehicle-treated) was used as reference group for pairwise comparisons.

Results
Body Weight

Figure 11:
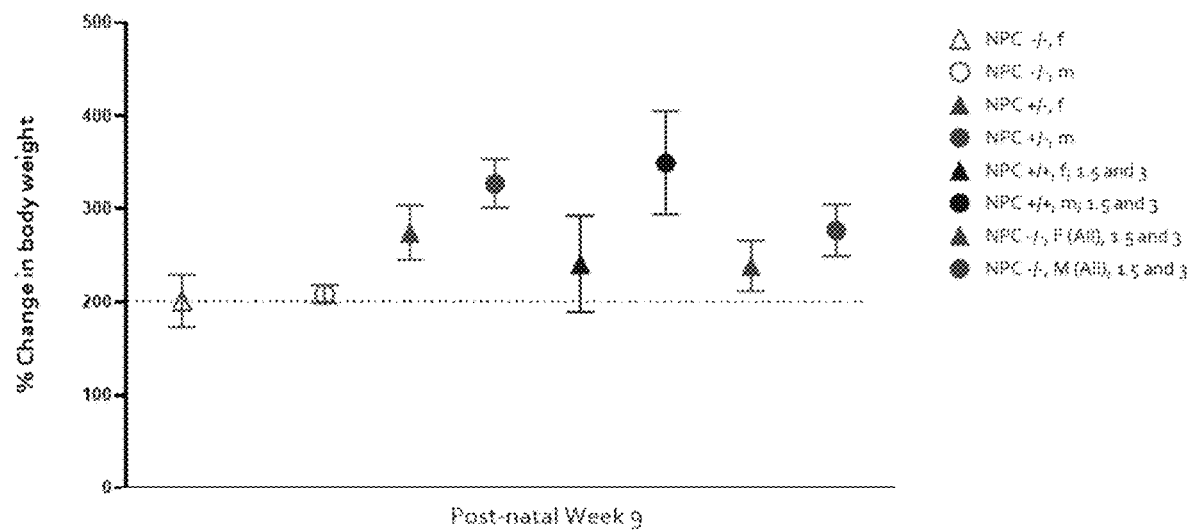
FIG. 11 shows a percentage change in mice body weights between post-natal day (PND) 11 and Week 9.

FIG. 11 shows percentage change in body weights between PND 11 and Week 9. Graph represents the progress of body weights [g] per group measured daily during the first treatment week and weekly thereafter.

The results show that general health of the animals, as indicated by average percent body weight gains, was not impeded by AZ-3102 and both genders of NPC (−/−) mice treated with AZ-3102 gained more than the NPC (−/−) untreated animals.

TABLE 8

Brain:plasma exposure ratios for AZ-3102 following repeat oral administration from PND 11-70.
Pharmacokinetics

| Parameter | Brain:Plasma Ratio | |
| --- | --- | --- |
| | Male | Female |
| $AUC_{0-24}$ | 0.95 | 1.37 |
| Cmax | 0.26 | 0.41 |

Glucosylceramide Levels

Figure 12:
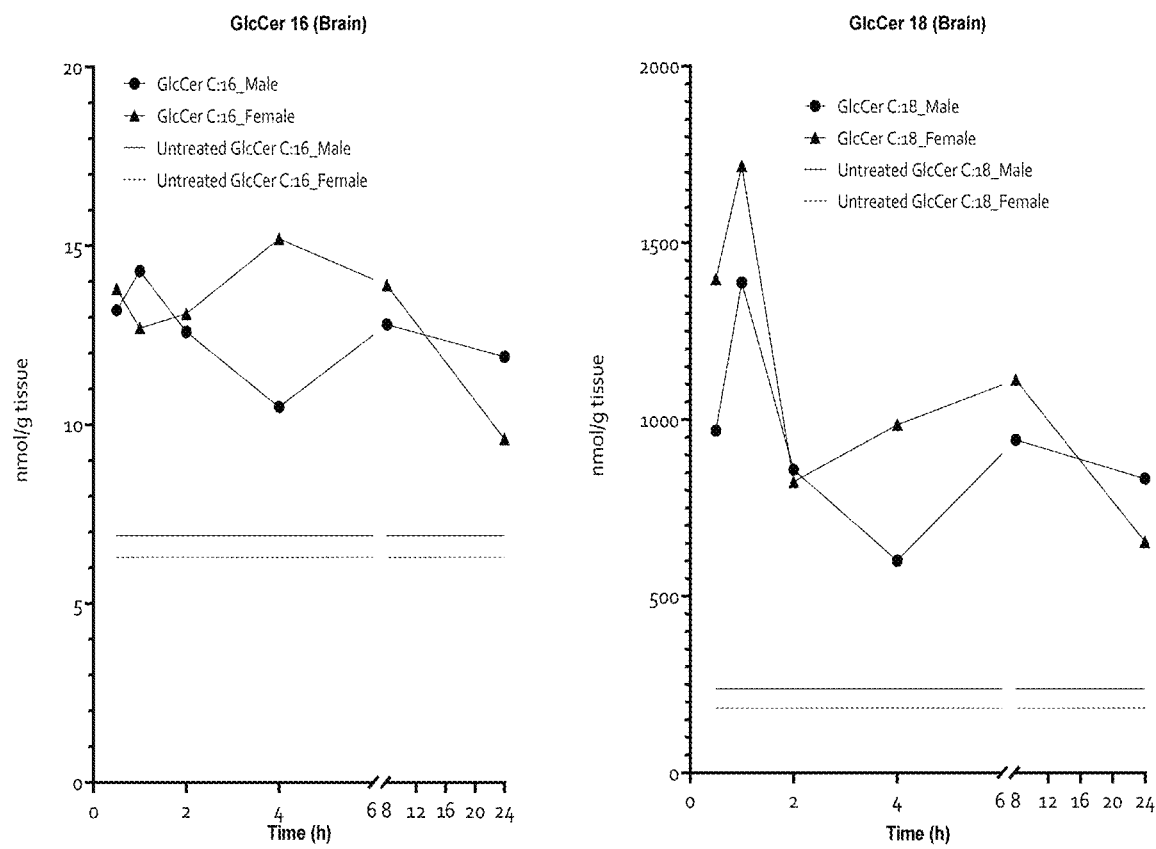
FIG. 12 shows glucosylceramide C16:0 and C18:0 levels following repeat oral administration from PND 11-70.

FIG. 12 shows glucosylceramide C16:0 and C18:0 levels following repeat oral administration from PND 11-70.

Mice treated with AZ-3102 show increased levels of glucosylceramide C16:0 and C18:0 in the brain.

Clinical Signs

Definitions of Clinical Scores and Humane Endpoints Clinical Signs were monitored on a daily basis starting at P45 until the end of the study (according to the template shown in FIG. 18). The parameters "weight loss", "general health", "clinical findings" and "line specific findings" were recorded and rated according to a score scale. The sum of this score was used for evaluation.

TABLE 10

| Tremor Score. Tremor Score | |
| --- | --- |
| Tremor Score | Description (The animal's tremor is observed while manually tilting the cage and/or while opening the cage under a workbench) |
| Line specific score 1; "slight incoordination, slight-moderate tremor": | The animal is still able to walk in a straight line. Animal has a mildly impaired gait (wobbly walk and slight tremor). |
| Line specific score 5; "high level of tremor, uncoordinated movement": | The animal is frequently unable to walk in a straight line while moving within the cage and has a more distinct impaired gait than with Score 1. Due to the strong tremor and loss of coordination, the animal will sometimes fall over. |

TABLE 10-continued

| Tremor Score. Tremor Score | |
| --- | --- |
| Tremor Score | Description (The animal's tremor is observed while manually tilting the cage and/or while opening the cage under a workbench) |
| Line specific score 10; "reduced righting reflex": | Animal shows the same symptoms as described under Score 5. Additionally, the animal takes a few seconds (approx. at least 2-3 seconds) to gain sternal recumbency after being turned on its back by the examiner. |

Figure 13:
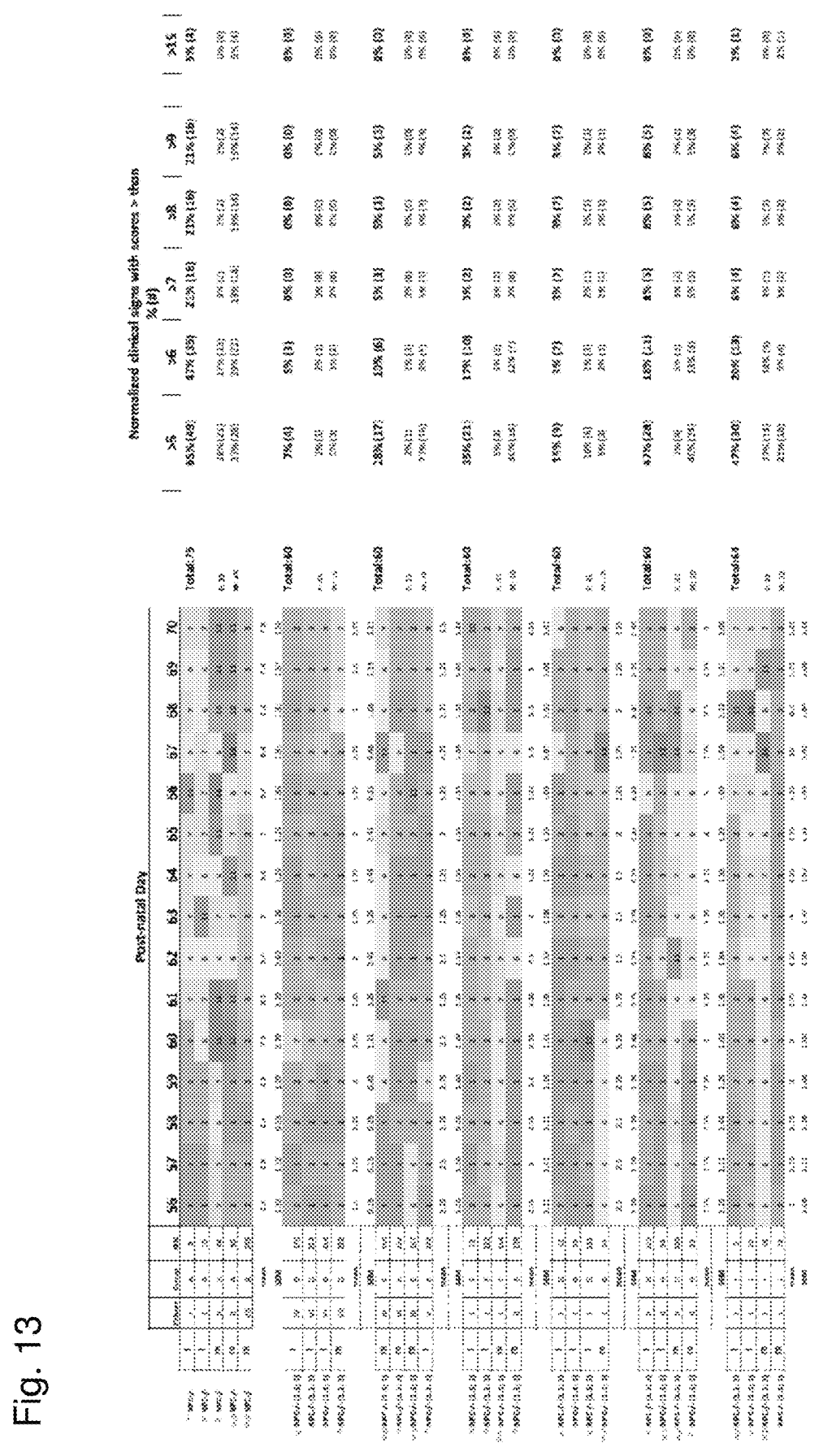

FIG. 13 shows a summary of the total clinical sign scores from PND 56-70 across all domains and by treatment group for each NPC (−/−) vehicle and AZ-3102 treated mice. Left side: total scores by animal and treatment group as visualized with a gradient, with lower scores in green and higher scores in red Right side: summary of scores reaching a numerical threshold. Threshold scores of greater than 7 are infrequent occurrences for treated groups; however, untreated groups had higher number total scores during the course of the study.

Figure 14:
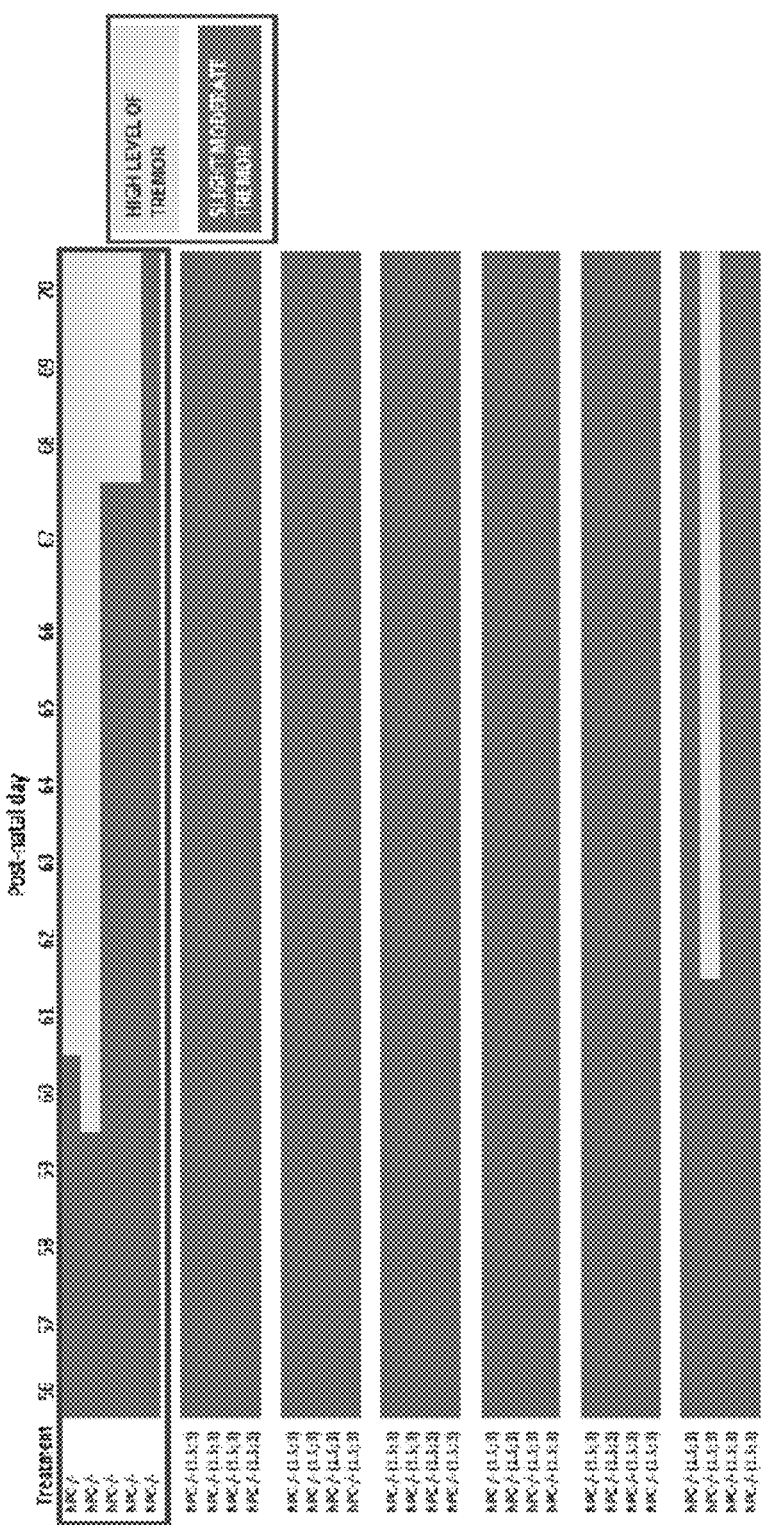
FIG. 14 shows tremor score from PND 56-70 in NPC (−/−) vehicle and AZ-3102 treated mice.

The results show that NPC (−/−) vehicle treated mice had a worsening (greater scores) in overall clinical signs compared to NPC (−/−) AZ-3102 treated animals. This is further shown in FIG. 13: right side in which scores of, for example, greater than 8, were more frequently observed in the NPC (−/−) vehicle treated group compared to NPC (−/−) AZ-3102 treated animals. Investigating these scores, we found that initiation, duration, as well as the strength, of tremor was also diminished by treatment with AZ-3102 (FIG. 14). High level of tremor was observed in all but one NPC (−/−) vehicle treated animals; whereas, AZ-3102 essentially eliminated this high level of tremor in all animals except one of the 24 animals tested.

FIG. 14 shows tremor score from post-natal day 56-70 in NPC (−/−) vehicle and AZ-3102 treated mice. Pink (=light grey) bars represent the appearance and duration of a high level of tremor (sore of 5); whereas the green (=dark grey) bars represent the appearance and duration of a slight or moderate tremor. With the exception of a single mouse in the untreated group, all other mice exhibited a high level of tremor (4 out of 5 mice). In contrast, only one mouse in the AZ-3102 treated group had a high level of tremor (1 out of 24). Possible tremor scores: 0: no tremor1: Slight incoordination, slight-moderate tremor; 5: High level of Tremor, uncoordinated movement; 10: Reduced righting reflex (no animal achieved this score).

Histological Results
Definition of Target Regions

Target regions were manually outlined by defining the region of interest (ROI) for the subsequent quantitative analyses of fluorescent labelling.

Readouts of Quantitative Analysis

The table presented below features four standard readouts.

Region size [$mm^2$]: These data show the average area per brain section covered by the target region. This information is important to verify proper sampling. It is also helpful to identify brain atrophy which is part of the phenotype of some animal models.

Immunoreactive area [%]: The percentage of the ROI that is covered by above-threshold immunoreactive objects (for example: cell somata, neurites, plaques); this is the most comprehensive parameter indicating whether there are overall differences in immunoreactivity.

Object density [number of objects per mm$^2$]: The number of above-threshold immunoreactive objects normalized to the size of the target area; this is especially useful to detect changes in neuronal density.

Object intensity [a.u.]: The average brightness of pixels of above-threshold immunoreactive objects; this indicates if there are differences in the cellular expression level of target proteins.

Object size [μm$^2$]: The size of above-threshold immunoreactive objects; this is useful to detect differences in activation of microglia or growth of plaques.

Calbindin-D28k

Immunofluorescence of Calbindin-D28k was detected with guinea pig polyclonal antibody, and the signal was quantified in the cerebellum and hippocampal formation. NCP(−/−) mice show strongly decreased Calbindin-D28k labelling compared to NCP(+/−) and NPC(+/+) mice. Treatment with test item significantly increased Calbindin-D28k in the cerebellum in all readouts. All effects are region-specific because no significant group differences were detected in the hippocampus.

Figure 16:
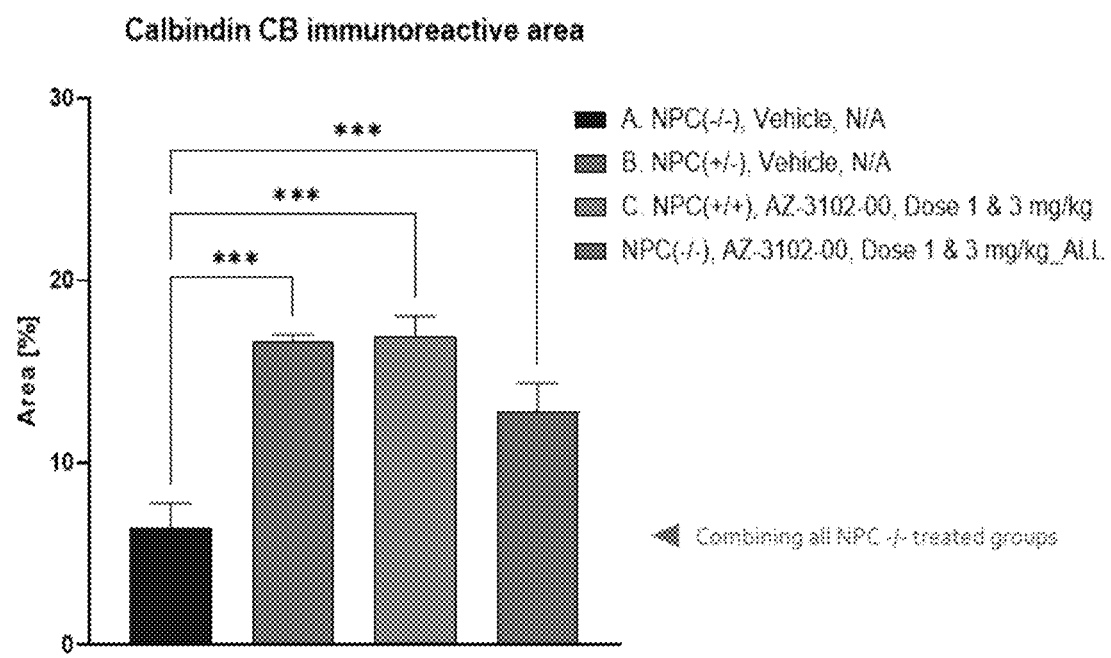
FIG. 16 shows brain immunohistochemistry: calbindin-D28k labeling in NCP(−/−) and NPC(+/−) vehicle treated mice compared to NPC (+/+, wild-type mice) and NPC (−/−) treated mice.
Figure 17:
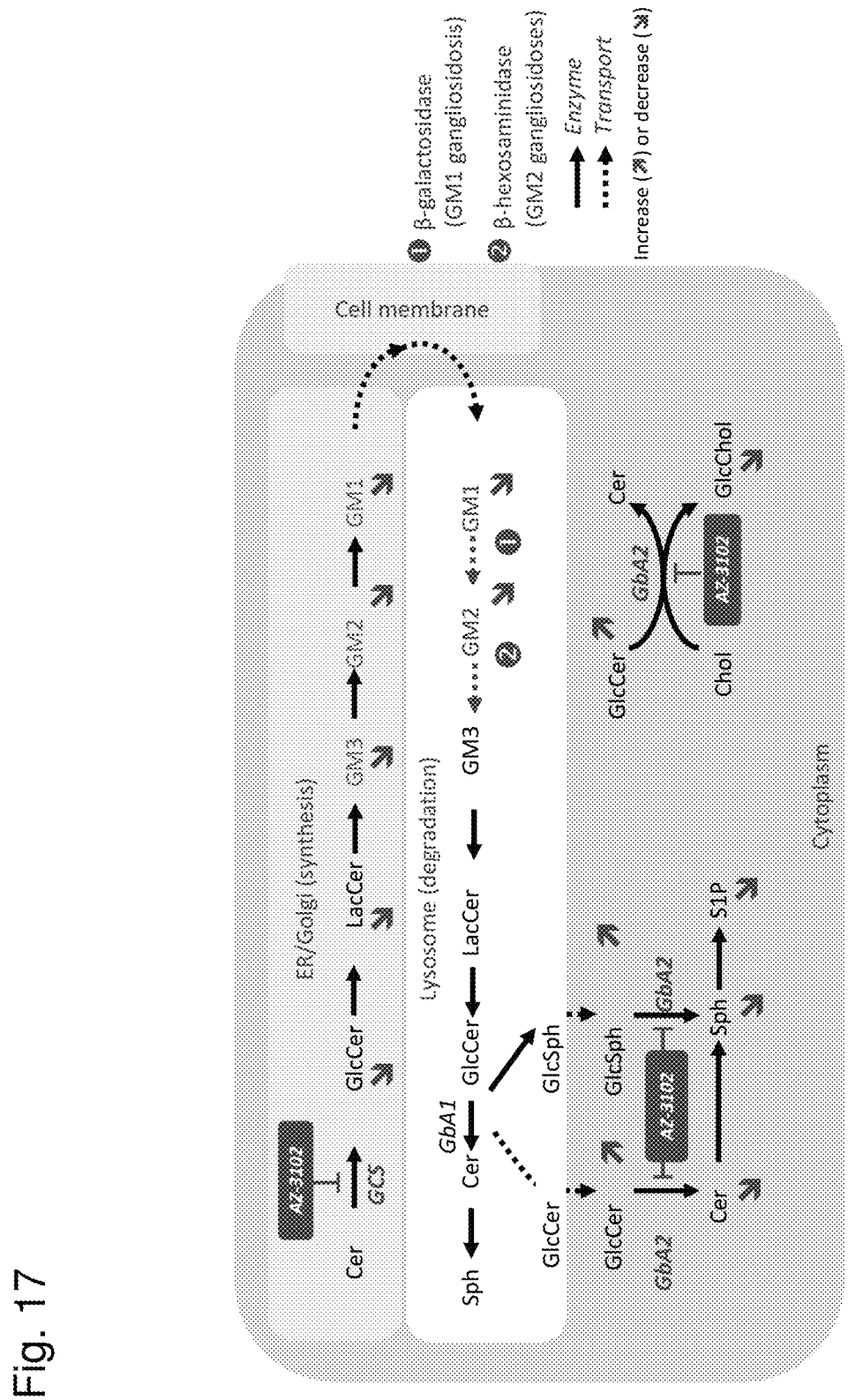
FIG. 17 summarizes the mode of action of the crystalline form of compound (I) (AZ-3102).

FIG. 16 shows the results of brain immunohistochemistry: calbindin-D28k labeling in NCP(−/−) and NPC(+/−) vehicle treated mice compared to NPC (+/+, wild-type mice) and NPC (−/−) treated mice. Graphs present the means of immunofluorescent signal measured within the ROI on 5 brain sections per mouse (n=2-4 per group). Data were analyzed by one-way ANOVA and Dunnett's post hoc test. Bar graphs represent group means+SEM. Bar graphs represent group means+SEM, *Adj. P-value: <0.001.

Employing immunohistological techniques using the cal-bindin-D28k marker for Purkinje cells, we found that AZ-3102 treatment, compared to vehicle treated NPC (−/−) mice, significantly limited cerebellar Purkinje cell loss (FIG. 16).

CONCLUSIONS

AZ-3102 is a novel oral small molecule being developed for a variety of lysosomal storage disorders. The unique mode of action of AZ-3102 lies with its high potency on glucosylceramide synthase (GCS), the non-lysosomal glucosylcerebrosidase (GbA2), as well as its brain-penetrant properties. AZ-3102 was investigated in a mouse model of Niemann-Pick type C disease [1, 2] in which mice, homozygous for the recessive NIH allele of the NPC gene, begin to lose weight and show tremor and ataxic gait at approximately 7 weeks of age [3]. Disease severity is associated with significant cerebellar Purkinje cell loss and clinical signs worsen until a humane endpoint is reached (typically at 12 to 14 weeks of age) [3]. In this study, we investigated daily oral dosing of AZ-3102 from post-natal day (PND) 11 to 70 to NPC (−/−), NPC (−/+) and WT (NPC (+/+); Balb/c) mice to assess its pharmacokinetic (PK) properties, ability to modulate glucosylceramide (GlcCer C16:0, GlcCer C18:0) and improve clinical signs. In addition, we also examined the treatment effect on an immunohistochemical marker for Purkinje cells which coincides with neuropathology. Following repeated daily oral dosing from PND 11-70, AZ-3102. General health of the animals, as indicated by average percent body weight gains, was not impeded by AZ-3102 and both genders of NPC (−/−) mice treated with AZ-3102 gained more than the NPC (−/−) untreated animals (FIG. 11). AZ-3102 demonstrated high brain:plasma exposures (Table 8) and consistent with AZ-3102 target engagement, increased GlcCer species measured from whole brain homogenates compared to vehicle treated animals by greater than 2-fold for GlcCer 16:0 and approximately 9-fold for GlcCer 18:0. These two GlcCer species are likely representative of other GlcCer species which would also be responsive to AZ-3102.

To evaluate whether AZ-3102 reaches sufficient brain concentrations to affect more specific signs of general health and neuropathology a variety of clinical signs were measured (Table 9). These scores, when summed over the observation period, provide a picture of health from PND 56-70. FIG. 13 is a graphical view of each animal per observed cohort over time. In this graphic, NPC (−/−) vehicle treated mice had a worsening (greater scores) in overall clinical signs compared to NPC (−/−) AZ-3102 treated animals. This is further quantitated in (FIG. 13: right side) in which scores of, for example, greater than 8, were more frequently observed in the NPC (−/−) vehicle treated group compared to NPC (−/−) AZ-3102 treated animals. Investigating these scores, we found that initiation, duration, as well as the strength, of tremor was also diminished by treatment with AZ-3102 (FIG. 14). High level of tremor was observed in all but one NPC (−/−) vehicle treated animals; whereas, AZ-3102 essentially eliminated this high level of tremor in all animals except one of the 24 animals tested. Employing immunohistological techniques using the calbindin-D28k marker for Purkinje cells, we found that AZ-3102 treatment, compared to vehicle treated NP—C(−/−) mice, significantly limited cerebellar Purkinje cell loss (FIG. 16). This finding has relevance to the Niemann-Pick type C in man, as neuronal death, and in particular Purkinje cells, as well as cerebral atrophy are hallmarks of the disease [4]. As cerebellar function is important for movement, the improved clinical signs and significant reduction in high level of tremor are likely a result of cerebellar Purkinje cell survival.

In summary, AZ-3102, an orally available, highly potent (nM) inhibitor of both GCS and GbA2, was able to penetrate the brain of NPC (−/−) and wild-type animals. Furthermore, AZ-3102 inhibited these enzymes in the brain as clearly shown through the modulation of GlcCer species, improved clinical signs, significantly reduced the high level of tremor, and limited the loss of cerebellar Purkinje cells compared to vehicle treated animals.

1. Loftus, S. K., et al., Murine model of Niemann-Pick C disease: mutation in a cholesterol homeostasis gene. Science, 1997. 277(5323): p. 232-5.
2. Zervas, M., K. Dobrenis, and S. U. Walkley, Neurons in Niemann-Pick disease type C accumulate gangliosides as well as unesterified cholesterol and undergo dendritic and axonal alterations. J Neuropathol Exp Neurol, 2001. 60(1): p. 49-64.
3. Santiago-Mujica, E., et al., Hepatic and neuronal phenotype of NPC1−/− mice. Heliyon, 2019. 5(3).
4. Vanier, M. T., Niemann-Pick disease type C. Orphanet Journal of Rare Diseases, 2010. 5(1): p. 16.

Example 5—Effect of Administration of the Crystalline Form of Compound (I) to Mice Suffering from Sandhoff Disease (Disruption of the Murine Hexb Gene [Hexb (−/−)] Through Mutations)

Mice suffering from Sandhoff disease were administered a therapeutically effective amount of AZ-3102. Initial data indicate that, similarly to treating Niemann-Pick type C, the clinical signs of diseased animals have improved.

The invention claimed is:
1. A crystalline form of compound (I),

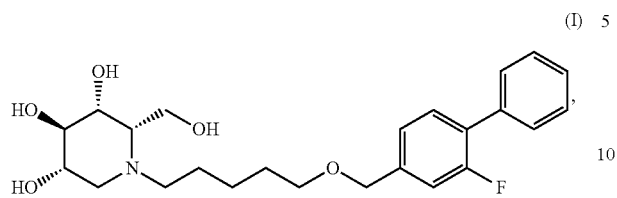

wherein the crystalline form displays a reflection, stated as a 2Θ value, at 17.8±0.2°, in an X-ray powder diffraction pattern, wherein the reflection at 17.8±0.2° is one of the four strongest reflections in the X-ray powder diffraction pattern.

2. The crystalline form of claim 1, further displaying one or more reflections, stated as a 2Θ value, at one or more of 4.1±0.2°, 8.3±0.2°, 12.4±0.2°, 13.6±0.2°, 14.5±0.2°, 14.9±0.2°, 15.2±0.2°, 17.2±0.2°, 19.3±0.2°, 21.2±0.2°, 22.4±0.2°, 22.9±0.2° and 23.3±0.2°, in an X-ray powder diffraction pattern.

3. A pharmaceutical composition comprising the crystalline form of claim 1.

4. The pharmaceutical composition of claim 3, wherein the pharmaceutical composition is contained in a capsule.

5. The pharmaceutical composition of claim 4, wherein the pharmaceutical composition is contained in the capsule:
   (a) without any other ingredient; or
   (b) with at least one pharmaceutically acceptable carrier.

* * * * *